(12) United States Patent
Rogers et al.

(10) Patent No.: US 8,898,798 B2
(45) Date of Patent: Nov. 25, 2014

(54) SYSTEMS AND METHODS FOR MEDICAL INFORMATION ANALYSIS WITH DEIDENTIFICATION AND REIDENTIFICATION

(71) Applicants: Robert Derward Rogers, Pleasanton, CA (US); Shahram Shawn Dastmalchi, San Ramon, CA (US); Darren Matthew Schulte, San Francisco, CA (US); Imran N. Chaudhri, Potomac, MD (US); Mary Ellen Campana, San Mateo, CA (US); Vishnuvyas Sethumadhavan, Mountain View, CA (US)

(72) Inventors: Robert Derward Rogers, Pleasanton, CA (US); Shahram Shawn Dastmalchi, San Ramon, CA (US); Darren Matthew Schulte, San Francisco, CA (US); Imran N. Chaudhri, Potomac, MD (US); Mary Ellen Campana, San Mateo, CA (US); Vishnuvyas Sethumadhavan, Mountain View, CA (US)

(73) Assignee: Apixio, Inc., San Mateo, CA (US)

( * ) Notice: Subject to any disclaimer, the term of this patent is extended or adjusted under 35 U.S.C. 154(b) by 238 days.

(21) Appl. No.: 13/656,652

(22) Filed: Oct. 19, 2012

(65) Prior Publication Data

US 2013/0124523 A1    May 16, 2013

Related U.S. Application Data

(63) Continuation-in-part of application No. 13/223,228, filed on Aug. 31, 2011.

(60) Provisional application No. 61/379,228, filed on Sep. 1, 2010, provisional application No. 61/682,217, filed on Aug. 11, 2012.

(51) Int. Cl.
*H04L 9/32* (2006.01)
*G06F 19/00* (2011.01)
*G06Q 50/24* (2012.01)
*H04L 29/14* (2006.01)

(52) U.S. Cl.
CPC .............. *G06F 19/32* (2013.01); *G06F 19/322* (2013.01); *G06Q 50/24* (2013.01)
USPC ............................................... 726/26; 726/28

(58) Field of Classification Search
CPC .. G06F 17/30616; G06F 19/322; G06F 19/32
See application file for complete search history.

(56) References Cited

U.S. PATENT DOCUMENTS

| | | | |
|---|---|---|---|
| 2008/0120296 A1* | 5/2008 | Kariathungal et al. | 707/6 |
| 2010/0117799 A1* | 5/2010 | Dormer et al. | 340/10.1 |
| 2010/0131299 A1* | 5/2010 | Hasan et al. | 705/3 |
| 2010/0169123 A1* | 7/2010 | Maus et al. | 705/3 |
| 2010/0324936 A1* | 12/2010 | Vishnubhatla et al. | 705/3 |

\* cited by examiner

*Primary Examiner* — Venkat Perungavoor
(74) *Attorney, Agent, or Firm* — Kang S. Lim

(57) ABSTRACT

A medical information navigation engine is useful in association with at least one electronic health record system. The engine decouples identifying information from clinical data from electronic health records. The clinical data includes clinical narrative having discrete data and textual data. The identifying information is stored. Additionally, the identifying information is associated with a token in the clinical data. The clinical data may then be indexed. The discrete data and the textual data in the clinical data may then be mined. Mining includes extracting at least one relevant event from the discrete data and the textual data. Next, the clinical data and identifying information may be reintegrated using the token. The event associated with the mined discrete data and textual data may then be exported. The system may also provide a validation tool for users, including clinicians, to search and view clinical data. The exported event may be used to alter treatment of a patient.

22 Claims, 17 Drawing Sheets

APIXIO

HCC Optimizer
Beta

Log out

Review Patient Opportunities

1500

Name: John Taylor  DOB: Jan. 2, 1930
0.162
Accepted RAF Value: 0.162   ID:
31382435                                    Total RAF Opportunity:

Diabetes without Complication              HCC: 19              0.162
 IM Office Visit                           May 19, 2010
 IM Progress Note                          Aug 23, 2010

Done with this patient?
Return to list

Version 0.05.2
© Apixio 2012

Log out

Document Review

```
Office Note                                              05/19/2010

Annual Exam 5/19/2010
CCDupload, Test 05/19/2010 9AM

Chief Complaint Annual Exam

HPI: Annual Exam- Patient doing well. Continues to do PT from her hip replacement. She is to see Dr. L in 3 weeks.
ROS: no headache, no changes in her vision, no CP, no SOB, no palpitations, no endocrine complaints, positive weight gain after surgery,
positive hip and back pain with radicular sx. Occ urine burning if doesnt drink enough water, positive easy bruising but normal coags preop, no
neuro sx, no vaginal symptoms- in fact she stopped using the cream Dr P recommended. Positive neuropathic pain in both legs, left more than
right. Derm stable.

PMH:
1- Dry macular degeneration
2- Aortic stenosis- Dr W echo 11/09 mild to mod AS with nl LV function
3- G4P3 post menopausal
4- Lichen sclerosis- vaginal- Dr B
5- Tubular adenoma on colo 12/08- due 2011
6- Hyperparathyroid- Dr T
7- Mild hearing loss
8- Bilat shoulder pain s/p corticosteroid injections Dr G
9- Bilat hip djd with worsening 9/09- MRI shows severe disease
10- Back pain with radiculopathy- MRI 9/09- Saw Dr G at ortho degenerative disease- no stenosis
11- Bells palsy x2
12- Hypothyroid
13- HTN
14- DM_ diet control
15- Atypical chest pain abnl stress test with Dr W but declines cath. Negative stress echo 5/09.
16- Osteopenia- intolerant of bisphosphantes- Dr T
17- S/p cholecystectomy for 30 yrs of upper quadrant pain, dr S. Had ERCP 10/08 for sphincterotomy. Endoscopy
18- Rheumatic Fever age 5
19- Peripheral neuropathy- Saw neuro Dr H 2007- DM vs idiopathic
20- GERD s/p endoscopy 2006 resolved
```

FIG. 16

SYSTEMS AND METHODS FOR MEDICAL INFORMATION ANALYSIS WITH DEIDENTIFICATION AND REIDENTIFICATION

CROSS REFERENCE TO RELATED APPLICATIONS

This continuation-in-part application claims priority to U.S. patent application Ser. No. 13/223,228, by Chaudhri et al., entitled "MEDICAL INFORMATION NAVIGATION ENGINE (MINE) SYSTEM", filed on Aug. 31, 2011, which application claims priority to U.S. Provisional Patent Application No. 61/379,228, by Ansari et al., entitled "MEDICAL INFORMATION NAVIGATION ENGINE (MINE) SYSTEM", filed on Sep. 1, 2010, which applications are incorporated herein in their entirety by this reference.

Also, this application claims priority to U.S. Provisional Patent Application No. 61/682,217, by Rogers et al., entitled "MEDICAL INFORMATION NAVIGATION ENGINE (MINE) SYSTEM", filed on Aug. 11, 2012, also incorporated herein in its entirety by this reference.

BACKGROUND

The present invention relates to medical information analysis systems and methods, and particularly to management and consolidation of medical information.

Despite rapid growth of innovation in other fields in recent decades, the world of medical information, including patient medical records, billing, and a host of other information, has enjoyed little to no useful consolidation, reliability, or ease-of-access, leaving medical professionals, hospitals, clinics, and even insurance companies with many issues, such as unreliability of medical information, uncertainty of diagnosis, lack of standard, and a slew of other related problems.

One of the challenges facing those in the medical or related areas is the number of sources of information, the great amount of information from each source, and consolidation of such information in a manner that renders it meaningful and useful to those in the field in addition to patients. Obviously, this has contributed to increased medical costs and is perhaps largely attributed to the field suffering from an organized solution to better aid the medical professionals, to better aid those requiring more reliable patient history and those requiring more control and access over such information.

Currently, when a patient sees various medical professionals over the years, there is no method for universally tracking recommendations, thoughts, prescriptions, diagnosis. This hinders the job of insurance companies in making certain requisite determinations, physicians making decisions that directly impact the health of the patient, and hospitals and other medical institutions that similarly rely but do not have the benefit of the requisite information, not to mention the patient.

Further, there are problems in the current medical system that are associated with patient identity in that due to the exposure of a patient to various medical associations/professionals over the years and the possibility of various ways of identifying the same patient, patients' records and identity are oftentimes compromised, creating a slew of problems both for the patient as well as those treating the patient.

Further, privacy of a patient's health records is not currently reliably maintained, as there are too many cases of health record compromises. Additionally, patient control of access to medical information is nearly nonexistent. Additionally, secure and remote access of medical information is currently lacking.

It is therefore apparent that an urgent need exists for a method and apparatus for managing medical information in a manner that is beneficial, reliable, portable, flexible, and efficiently usable to those in the medical field, including patients.

SUMMARY

To achieve the foregoing in accordance with the present invention, to overcome the limitations in the prior art described above, and to overcome other limitations that will become apparent upon reading and understanding the present specification, the present invention discloses a method and a corresponding structure for transacting medical information.

In some embodiments, a medical information navigation engine is provided which is useful in association with at least one electronic health record system. The system may decouple identifying information from clinical data from electronic health records. The clinical data includes clinical narrative having discrete data and textual data. The identifying information is stored separately in an encrypted manner. Additionally, the identifying information is associated with a token in the clinical data.

The clinical data may then be aggregated. The discrete data and the textual data in the clinical data may then be mined. Mining includes extracting at least one relevant quality measure from the discrete data and the textual data. The mining may also include extracting concepts and facts about the patient such as conditions or biometric values or facts about clinical services performed for the patient such as surgical procedures or from the discrete data and the textual data, used for the computation of eligibility for a clinical quality or performance measure.

Next, the clinical data and identifying information may be reintegrated using the token if required by the application. Reintegration may be employed if the application is involved with a particular patient versus a population. Moreover, when additional information needs to be meta-tagged for a specific patient or additional data needs to be added to a specific patient, reintegration may be employed; potentially followed by a subsequent deidentification (decoupling of the patient identifying information from the clinical data) step. The quality information associated with the mined discrete data and textual data may then be exported. The system may also provide a validation tool for users, including clinicians, to search and view clinical data. The exported quality information may be used to alter treatment or change the eligibility of a patient.

In addition, it may be desirable to reintegrate a group of patients for a particular application. For example, identifying a group of patients whose demographics (e.g., age, sex, race), genotypic (e.g., genetic markers for pathologies), or phenotypic (e.g., medical conditions) qualify them for a clinical trial.

The system may also provide a view including patient disease, patient condition, patient risk stratification, patient care quality measure compliance, and/or patient actionable care gap. The patient risk stratification includes co-morbidities associated with the patients. The system may identify at least one coding or documentation opportunity associated with patient conditions mined from unstructured clinical data, where the patient condition has not yet been associated with one of the patient claims.

These and other objects and advantages of the invention will no doubt become apparent to those skilled in the art after having read the following detailed description of the preferred embodiments illustrated in the several figures of the drawing. Note that the various features described above may be practiced alone or in combination. These and other features will be described in more detail below in the detailed description of the invention and in conjunction with the following figures.

BRIEF DESCRIPTION OF THE DRAWINGS

In order that the present invention may be more clearly ascertained, some embodiments will now be described, by way of example, with reference to the accompanying drawings, in which:

FIGS. 14-16 illustrate exemplary screenshots for the analysis of medical information, and application of said analysis to individual patients, in accordance with some embodiments.

DETAILED DESCRIPTION

Figure 1:
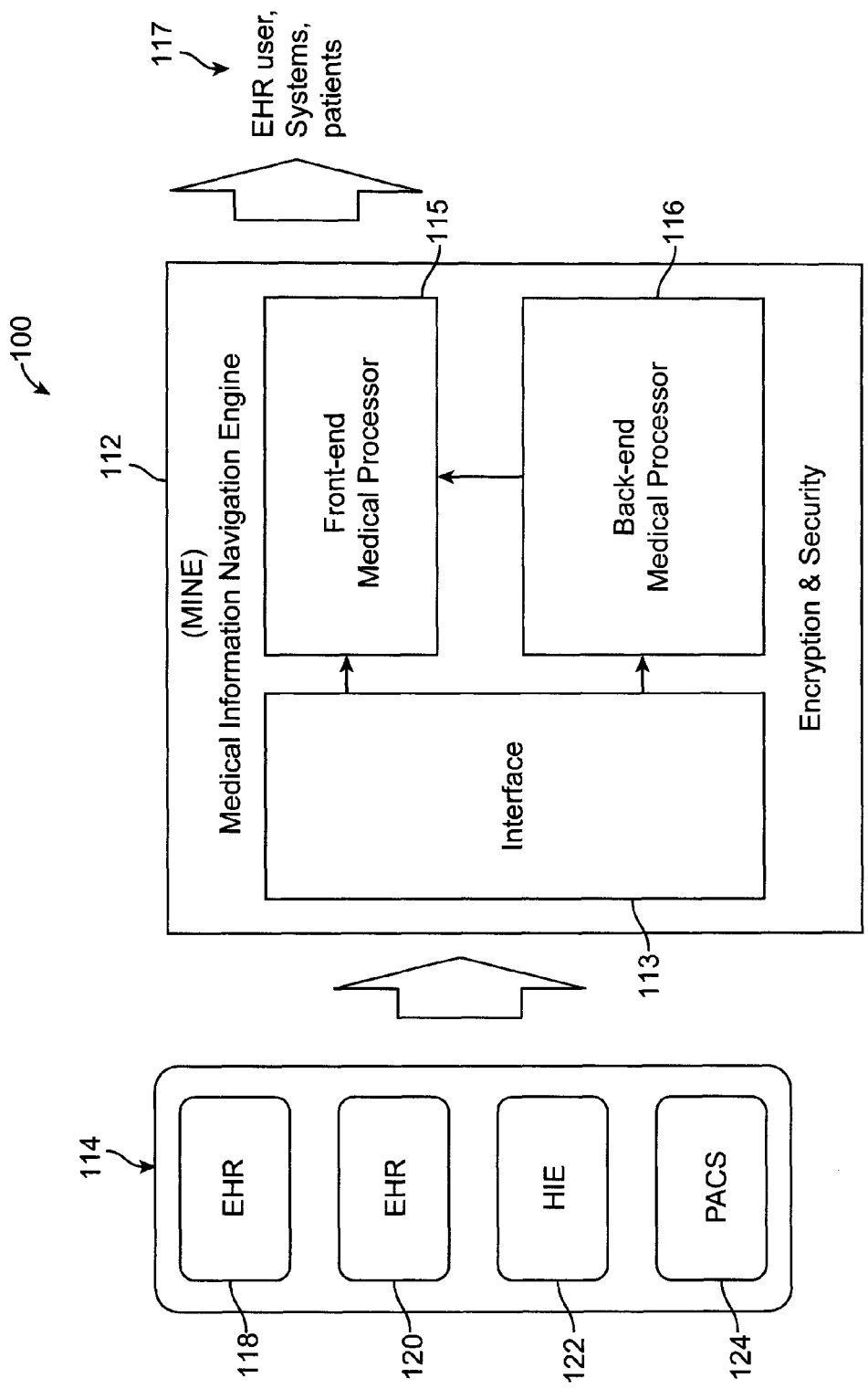
FIG. 1 shows a medical system 100 including a medical information navigation engine (MINE) 112, in accordance with some embodiments.

The present invention will now be described in detail with reference to several embodiments thereof as illustrated in the accompanying drawings. In the following description, numerous specific details are set forth in order to provide a thorough understanding of embodiments of the present invention. It will be apparent, however, to one skilled in the art, that embodiments may be practiced without some or all of these specific details. In other instances, well known process steps and/or structures have not been described in detail in order to not unnecessarily obscure the present invention. The features and advantages of embodiments may be better understood with reference to the drawings and discussions that follow.

While Healthcare organizations today are struggling with use of greater volumes of digitized patient data stored in various formats across disparate systems. Most data created in clinical applications is textual and not computable by information systems. The inability to efficiently retrieve knowledge not only limits efforts to improve patient safety and outcomes, but also leads to missed quality and financial objectives.

In accordance with some embodiments, the system disclosed herein may integrate and intelligently analyze structured and unstructured information that resides across a healthcare organization. A medical Information Navigation Engine (MINE) may include a virtual Health Information Exchange (HIE) platform and Clinical Knowledge Exchange™ (CKX) CKXREF, thereby enabling healthcare organizations to fill the knowledge gaps created by disparate and poorly connected computer systems and clinical information largely represented in textual form. MINE also provides Semantic Tagging and Reconciling of an integrated patient data set by the CKX CKXREF to make information accessible and actionable by clinical, administrative and financial systems.

In some embodiments, Data access and analytics modules enabling organizations to improve the quality of patient care while lowering costs and optimizing reimbursements, including modules such as a Patient Analyzer, a Population Analyzer, a Quality Optimizer, and a HCC Optimizer.

The CKX platform CKXREF and its modules may be web-based, thereby reducing IT operations overhead for managing servers, simplifying account activation, reducing deployment times, and user administration processes.

The Medical Information Navigation Engine offers a technology solution to the information overload problem by presenting a unique interface to both structured and unstructured data.

The proliferation of electronic health records among providers, and government initiatives, have caused explosive growth in the volume of clinical data. Large amounts of both structured data, such as coded lab tests and procedures; and unstructured data, such as encounter notes and transcriptions is available to providers. Solutions for meaningful ways of navigating the data and preventing information overload are critical for health care providers to enhance care quality.

MINE enables providers to enter free text queries as they would with any search engine and returns medically relevant results across both structured data and unstructured data. Using advanced natural language processing (NLP) technology to understand the intent behind the queries typed by the user, MINE is able to return the most relevant results to that query.

The following description of some embodiments will be provided in relation to numerous subsections. The use of subsections, with headings, is intended to provide greater clarity and structure to the present invention. In no way are the subsections intended to limit or constrain the disclosure contained therein. Thus, disclosures in any one section are intended to apply to all other sections, as is applicable.

I. Medical System

Referring now to FIG. 1, a medical system 100 is provided, in accordance with an embodiment of the invention. The system 100 is shown to include medical source 114, a medical information navigation engine (MINE) 112, and medical information consumers (also referred to herein as "output" or "medical output") 117. The medical source 114 are shown to include more than one electronic health record (EHR) 118 and 120, health information exchange (HIE) 122, and a picture archiving and communication system (PACS) 124. The MINE 112 is shown to include interface 113, a backend medical processor 116, and a front-end medical processor 115. Depending on the implementation, processors 115, 116 can be distributed, e.g., using cloud computing. Processors 115, 116 can also be combined.

"Medical information", as used herein, refers to any health-related information, including but not limited to patient medical records, patient entered information, care team entered information, healthcare or wellness device generated information, and billing information.

The source 114 generally generates and provides various medical information to the MINE 112. For example, the EHRs 118 and 120 each may provide information such as medical records and billing, the HIE 122 may provide information such as medical records, and the PACS 124 may provide information such as diagnostic imaging and reports.

The medical information consumers 117, which may be made of a host of entities or individuals, such as patients, clinics, medical institutions, health organization, and any other medical-related party, use information that is provided by the processor 115 of MINE 112 and that can, by way of example, consist of patients, medical systems, medical organization administrators, medical researchers, and/or EHR users. These medical information consumers may access information directly from MINE or indirectly via other third party systems. Examples of such third party systems include but not limited to quality reporting systems, population management systems, financial systems, and so on. For example, user-customized processed medical information is provided by the processor 115 to a number of users within the medical information consumers 117. In this case, the processor 115 generates user-customized processed medical information to a plurality of users, with at least a portion of the user-customize processed medical information being provided to each of the users based on the relevancy of the portion being provided of each user's specific function or role and each user's associated security privileges.

The processor 116, in some embodiments, indexes identifies, maps, and consolidates medical information, received from the interface 113, and tags this information, and determines to reconcile the tagged information. In some methods and embodiments, information that is extracted from images is tagged to enhance recall of search queries. Indexing, at least in part, processes document and converts them into formats that allows for quick searching across a large collection of documents.

The information in the MINE 112 is encrypted and secure both in transit and at rest via multiple security protocols to ensure privacy of sensitive medical information.

It is understood that the sources 114 of FIG. 1 includes merely some examples of the sources that communicate with the MINE 112 and that other sources, known to those in the field, are contemplated. Similarly, the output 117 may be used by those or entities not discussed herein but that are contemplated and within the scope and spirit of the invention.

The interface 113 serves to receive information that is in various forms, such as but not limited to text, html, CCD, CCR, HL7, pdf documents, word documents, scanned documents, images, general XML documents and any other type or formatted information. The interface 113 then provides to the processors 115 and 116 information, as needed.

The processor 116 receives some of the medical information that the interface 113 processes and performs certain tasks to process it, such as indexing, semantic meta-tagging, and reconciliation. Indexing takes processed documents and converts them into formats that make it easy to quickly search across a large collection of documents. Semantic meta-tagging embeds information into the medical information that is relevant thereto and that can be later used to search for certain information for the purpose of reconciliation and search, among many others.

One aspect of consolidation, reconciliation and deduplication, generally refers to removing of redundant patient medical records, such as, multiple records for the same individual appearing as though the records are for different individuals or multiple data elements that are recorded similarly but slightly differently in the different sources. In this case, the processor 116 recognizes that the records belong to a single individual or are the same data and just recorded differently and automatically consolidates them. The patient or a user of the system 100 may also manually perform reconciliation. Whether or not reconciliation is performed is advantageously determined by the processor 116.

The processor 116 outputs the indexed, tagged and reconciled information to the front end processor 115. The foregoing tasks are a generalization and further details of each are provided below.

The processor 115 performs certain tasks on the information provided by the interface 113 and the processor 116, which include query, search, presentation, and quality checking The output of the processor 115 is the output of the MINE 112, or output 117.

The MINE 112, through the processor 115, in some embodiments and methods, invites members of a medical care team to join it thereby allowing distributed user-organized care teams.

Querying, as performed by the processor 115, is the ability to receive, as input, a free text query, from a user, (i.e., a query without any restrictions on the structure)—and converting the free text query into commands to a medical search engine, such as Medical Lexical Search Engine and the MATRIX (Medical Application Terminology Relationship IndeX) Concept Search Engine, using a sophisticated query processing engine optimized to work with medical queries. The results of the search engine are sent to the presentation display planner—which decides the most relevant presentation given the user's organization and role (e.g., the provider, search query program, a healthcare administrator, a study administrator, and the patient). The presentation discussed below, receives such information. In some embodiments and methods, the medical information or user information is processed to suggest relevant queries.

Search, as performed by the processor 115, is built around the concept of Zero-Click Relevance—or the ability to get to all the relevant information an actor in the healthcare system requires by typing in just a single query. The search engine, within the processor 115, performing the search comprises an indexing and searching, as will become apparent shortly. Optionally, search results may be securely embedded into third party programs. In some embodiments, searching involves determining presenting (also referred to herein as "providing") access to specific relevant data based on a search query, the patient, and the user's specific function and/or role and security privileges. A user may be within the output 117 and security privileges are either determined by the MINE 112 or by the patient or both. Information, uploaded to the MINE 112, by users, such as output 114, in some embodiments, is searched by the processor 115. The uploaded information may include information such as but not limited to status posts, records, and images. Such user-uploaded information is routed automatically to the output 117, as needed.

Some aspects of the search are now discussed relevant to an example. Assuming, by way of example, that general practitioner Dr. Smith's new patient, Joan Sample, has a complaint of chest pain. Joan has brought several CCDs and a 600-page pdf file of her chart. She has seen a cardiologist who uses NextGen and a G.I. specialist whose charts are in e-MDs, and has visited the emergency room. Dr. Smith uses the search of the various methods and embodiments of the invention to efficiently assemble the relevant information he needs. Dr. Smith selects Joan Sample as the patient and enters the clinical context "chest pain" in the search bar of a screen presented by the MINE 112. He is presented with relevant lab results, such as CKMB and Amulase, relevant diagnostic results, such as EKG and chest CT scan, and all progress notes and consult reports in which concepts relevant to chest pain, like "GERD" and "Holter monitor", are mentioned. Two distinct types of searches are combined, in accordance with some embodiments, to retrieve information medically relevant to Joan's complaint: 1) Lexical search, where text in the patient record is searched for occurrences of the search term, its variants and synonyms; and 2) Medical concept search, where data that is medically related to the search term is retrieved. Medical concept search finds relevant structured data with standardized codes, such as lab results, and text results, such as progress notes, which include terms medically related to the search term. In Joan's case, a search for "chest pain" returns a CKMB lab result and a reference to a chest CT scan. Accordingly and advantageously, the Lexical and Medical concept search solves Dr. Smiths' information overload problem by returning information in the chart most relevant to Joan's chest pain complaint. Further, in some embodiments, the presentation, discussed shortly, presents a united view of Joan's history by reconciling and de-duplicating data from multiple sources that may be coded and described differently. Redundant data is automatically reconciled even if it is described differently by differently sources.

Presentation, as performed by the processor 115, is displaying health information to the requesting user in a way that reduces the number of clicks and maximizes the amount of meaningful information delivered based on the interpreting the intent of the user query.

Quality checking, as performed by the processor 115, is checking of the quality of medical information provided by various sources, i.e. source 114, by the patients, structured data, and unstructured data, in a Wiki-like mannered setting whereby the users can help maintain and improve the quality of information displayed. The foregoing tasks, performed by the processor 115, are further described in detail below. Additionally, the users or patients may make comments regarding medical information, in a Wiki-like manner.

In summary, the MINE 112 transacts medical information including the interface 113 receiving medical information from a number of medical sources (such as within the source 114) for processing, identifying, mapping, and consolidating by the medical processor 116, providing access to specific relevant data, based on a user's security privileges, within the identified, mapped, and consolidated medical information, based on user-specific functions or roles, performed by the processor 115, and generating user-customized processed medical information to a number of users, such as within the output 117, with at least a portion of the user-customized processed medical information being provided to each of the users based on its relevancy to each user's specific function or role and each user's associated security privileges.

Figure 2:
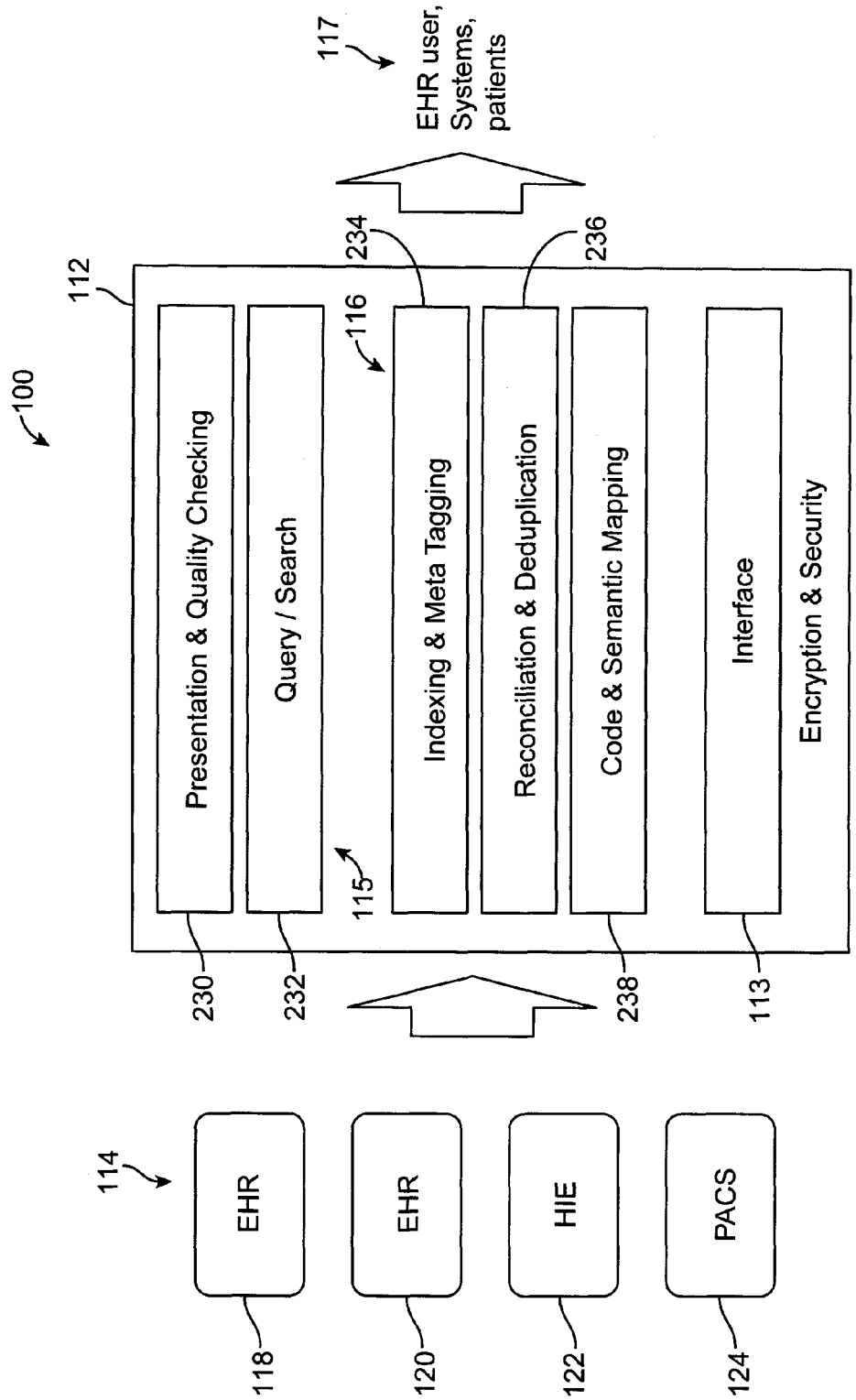
FIG. 2 shows further details of the MINE 112 of FIG. 1, in accordance with some embodiments.

FIG. 2 shows further details of the system 100, particularly the MINE 112 thereof. That is, the processor 116 is shown to include an indexing and metal tagging module 234, which includes an indexing module and a meta tagging module (both of which are not shown in FIG. 2 in the interest of clarity), which may be a module, as shown in FIG. 2 or two physically separate modules. The processor 116 is further shown to include a reconciliation and de-duplication module 236, which also can be broken out into two modules, a reconciliation module and a de-duplication module, and a code and semantic mapping module 238, which also may be a single module or multiple modules. The modules 234, 236, and 238 communicate with one another.

The processor 115 is shown to include a presentation and quality checking module 230, which may be a single module or broken out into two modules, and a query and search module 232, which also may be separate or combined modules. The modules 230 and 232 communicate with each other and with the modules of the processor 116. The interface 113 communicates with modules of both processors 115 and 116 and is essentially a gateway into the MINE 112 from the sources 114.

The foregoing modules may be software programs, executed by a computer or computing engine of suitable sorts, or may be implemented in hardware (as will be described in greater detail below in reference to FIGS. 17A and 17B).

Figure 3:
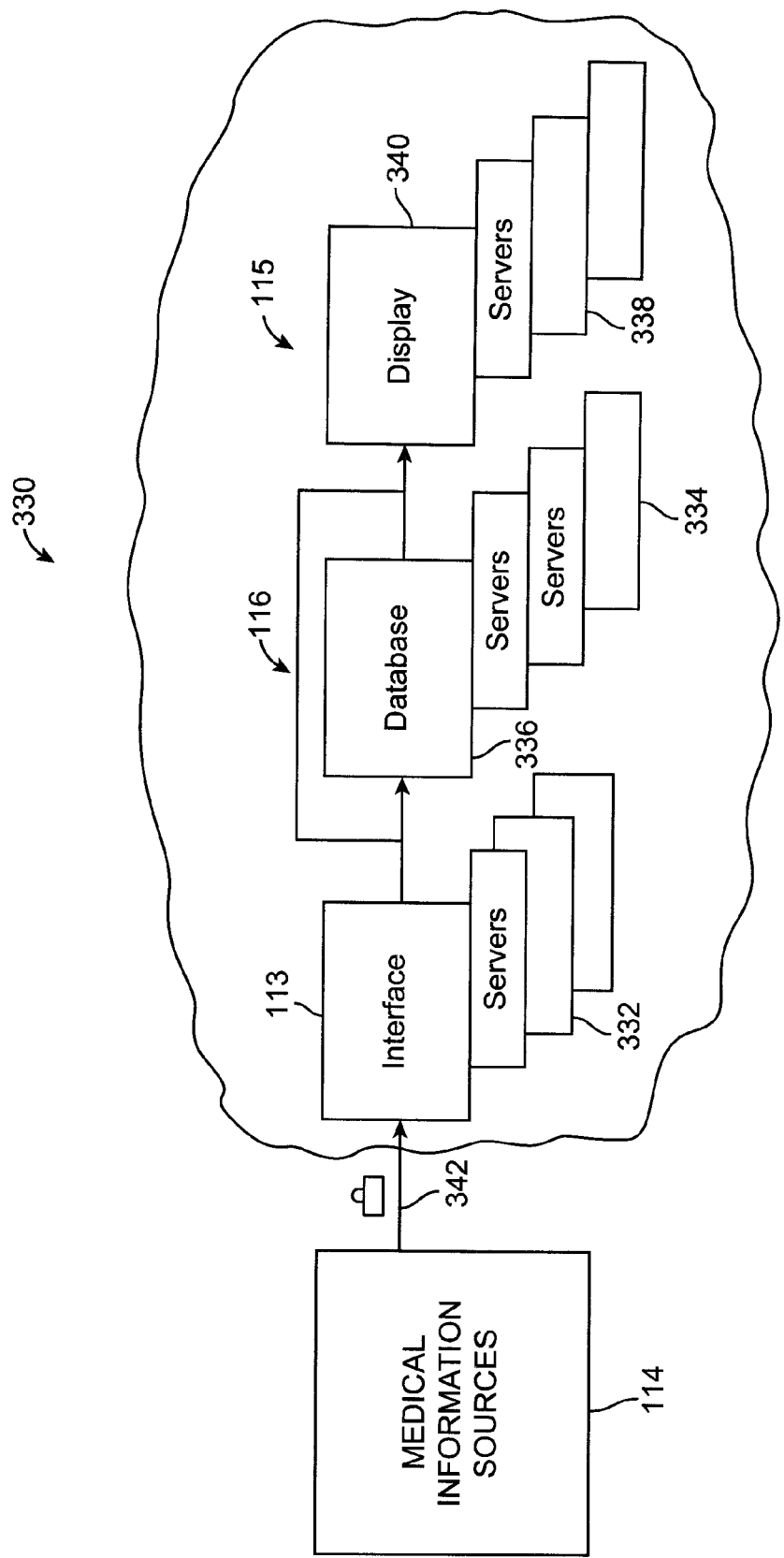
FIG. 3 shows an exemplary embodiment implementing the system 100 using various devices, in accordance with some embodiments.

FIG. 3 shows an exemplary embodiment implementing the system 100 using various devices. That is, the medical system 330 is analogous to the system 100 and is shown to include the sources 114 coupled to communicate, securely, through the secure communication link 342, to the interface 113. The link 342 may be any suitable communication channel allowing information of various formats and types, to be transferred to the interface 113 in a secure and encrypted fashion. Exemplary communication channels of which the link 342 is made include the Internet, VPN connections over the Internet, private dedicated digital lines such as T1, T3, E1, E3, SONET, and other fiber optic formats.

The interface 113, in some embodiments, is a software program that executes on one or more servers 332, which can be a server of any kind of suitable computing engine, such as personal computer (PC). The servers 332 receive secure information through the link 342 from the sources 114. The processor 116, in some embodiments, includes a database 336 and one or more servers 334, which may be any suitable computing engine, similar to the servers 332, including but not limited to PCs or servers.

The database 336 and servers 334 perform the tasks discussed above relative to the processor 116 and the display 340 and servers 338 perform the tasks discussed above relative to the processor 115 though these processors may and often perform additional tasks related to medical information, some examples of which are presented and discussed below and the rest of which are contemplated and achieve the various advantages, results and functions presented herein.

The processor 115, in some embodiments, includes display and visualization 340 executing on one or more servers 338, which may be any suitable computing engine, similar to the servers 332, including but not limited to PCs or servers. The display 340 is used to construct presentation and display information to users, such as the patient's records, billing information, and other types of medical information. The display 340, in some embodiments, also performs processing of some of the functions of the processor 115.

As shown in FIG. 3, the servers 332 are coupled to the database 336 and the servers 334, and to the display 340 and the servers 338 and the database 336 and servers 334 are coupled to the display 340 and the servers 338.

In some embodiments, the interface 113, servers 332, database 336, servers 334, display 340, and servers 338 are remotely located relative to the sources 114 and in some embodiments, remotely located relative to one another. Further, they are considered a part of the Internet cloud where, performing their tasks in a manner known as cloud-computing. However, other manner of achieving the functions and advantages of the invention, including various other of implementation, not shown in FIG. 3 or other figures herein and/or not discussed are contemplated.

Figure 4:
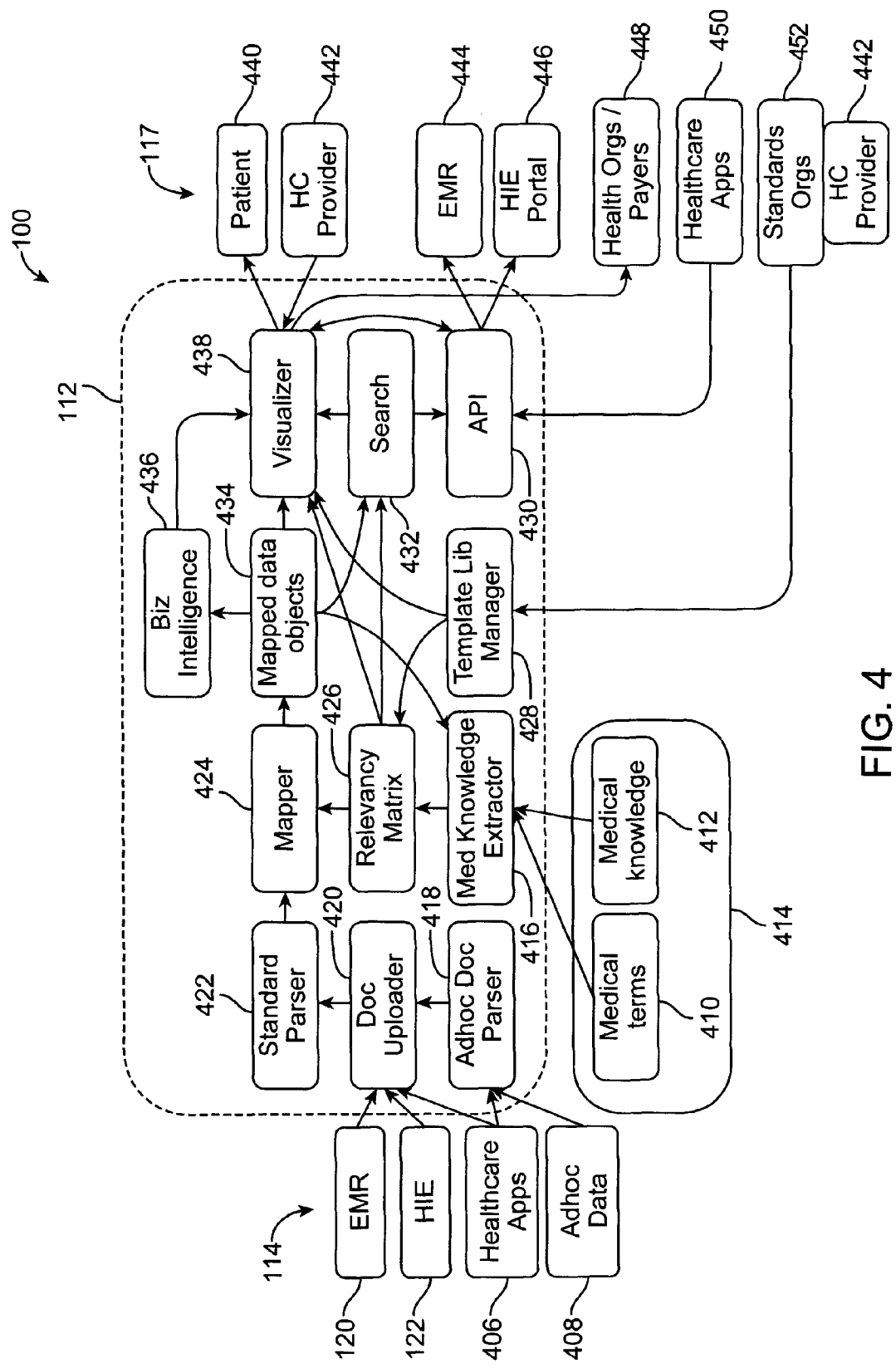
FIG. 4 shows further details of the system 100, in accordance with some embodiments.

FIG. 4 shows further details of the system 100, in accordance with an embodiment of the invention. The system 100 is a block diagram of thereof with arrows shown linking the blocks to one another. It is understood that these arrows represent data flow between blocks and merely examples of some of the data flows and not all-inclusive thereof.

The system 100 is shown to include medical sources 114, MINE 112, which is analogous to MINE 112 of FIG. 1 with additional details shown, medical output 117, medical source 114, and medical input 414. The source 114 is analogous to the source 114 of FIG. 1 except that it is shown to include electronic medical record 120, HIE 122, healthcare applications 406 and an ad hoc data block 408. The output 117 is analogous to the output 117 of FIGS. 1 and 2 except that it is shown to include the patient 440, the health care (HC) provider 442, the EMR 444, the HIE portal 446, healthcare Apps 450, Standards Orgs 452, and Health Orgs/Payers 448. The input 414 is shown to include the medical terms 410 and the medical knowledge 412, which are input to the MINE 112.

The MINE 112 is shown to include a standard parser 422, a document uploader 420, an ad hoc document parser 418, a mapper 424, a relevancy matrix 426, a medical knowledge extractor 416, a mapped data objects block 434, a business intelligence block 436, a template library manager block 428, an Application Programming Interface (API) 430, a search module 432, and a visualizer module 438, which are some of the blocks/functions performed by the MINE 112 while others are contemplated to achieve the various functions and advantages discussed herein.

The search module 432 performs functions discussed hereinabove and other functions that will become further clear with subsequent discussions. Similarly, the visualizer module 438 performs the functions discussed above with further details provided in subsequent discussions. The parser 418, the uploader 420, and the parser 422 provide the capability of the MINE 112 to accept information, in a variety of different formats such as a collection of medical records, in standard and ad hoc forms, by the source 114. For example, the ad hoc data block 408 may provide information to the MINE 112 in ad hoc form, which the parser 418 decodes or parses for use by other blocks of the MINE 112.

The extractor 416, the matrix 426, and the mapper 424 serve to collectively collect medical knowledge and identify, extract and map multidimensional relationships within them. Multidimensional relationships are between different types of medical data such as concepts, labs, problems, vital, medications, allergies as well as different types of relationships between the medical data such as "has comorbidity with" and "cures" for a drug. For example, implicit to these multidimensional relationships may be drug relevancy to a particular pathology. For example, it is known that Abilify® may cause diabetes. These "strengths of association" may be utilized to build causality/relevancy relationship models by the mapper 424. These relationships may then be stored in the relevancy matrix for later analysis. In some embodiments, the system may select which relationships to return in a particular application. This may be adjusted by the system on the fly in order to provide a user with the most relevant analytics and information. For example, a user querying a term like "diabetes" will likely return only tightly associated results, because otherwise the search would be too broad and render it meaningless. However, within labs and/or medications looser associations may be permitted in order to improve the systems utility.

These multidimensional relationships are embodied in the relevancy matrix 426. The block 434 serves to combine medical records with their relevancy to specific medical concepts. For example, the specific medical concept of diabetes is related to the labs for hemoglobin al c and glucose results, to the medical concept of diabetic retinopathy, the diagnosis of foot sores, the medications of Metformin and insulin among other things. The module 438 serves to perform the functions of relevancy and reconciliation and presentation, as described hereinabove. The business intelligence block 436 can mine the collected data for trends and predictive capabilities that might be of interest to large health organizations and payers 448. The collected data can be mined/analyzed/observed/reported on, in aggregate form. Other organizations that could make use of the data are any organizations interested in monitoring or required to report quality metrics such as integrated delivery networks (IDNs), health plans and/or accountable care organizations (ACO). An example of business intelligence queries includes selecting an arbitrary cohort population for search of quality measures such as "show me all patients' information within my panel with diabetes with hemoglobin a1c high in the last six months".

The sources 114 provides medical information to the MINE 112, through a secure link, as noted previously. Within the medical information received by the MINE 112 generally is medical data or medical records. Before it is received by the MINE 112, medical data is created in a multitude of systems including the EMR 120, healthcare applications 406, and many other ad hoc data sources 408 (such as but not limited to the application, Microsoft Word). The data, which is typically aggregated in a HIE 122 and EMRs 120 can also be received by MINE 112. Structured data is increasingly becoming available in standard 'xml' formats such as continuity of care records (CCR), continuity of care documents (CCD), clinical data architecture (CDA), and other HL7 related standards. Ad hoc data is available in multiple formats such as word, pdf, fax, and image data. The collection of medical records from multiple sources creates a serious data duplication problem in the current medical environment. Much of the data from these sources may represent the same type of information or even the same instance of information with slightly different variations or completeness (e.g., Patient name with and without the middle initial or a drug labeled as a generic or brand name with or without a start date). The MINE 112 advantageously reconciles the same data instances for reconciliation purposes from different sources and identifies similar data instances for comparison purposes.

As opposed to typical health information exchange (HIE) where patient information is available to all the participants in the system, in the system 100, patient data is shared in a granular patient centric style to accommodate privacy and security on a per patient "need to know" basis based on the roles and needs of the users and their organizations. Examples of the "need to know" basis of information distribution include the following: (1) Some organizations such as those with healthcare providers may receive patient demographics in addition to the other medical information. (2) Other organizations such as sponsors may receive only the problem that the healthcare provider is interested in. (3) Still other organizations, such as study clients may just receive a count of patients that could fit a study candidate criteria and the be able to message those patients anonymously. The whole user interface presented by the presentation module 230 can change based on the rights and type of user. Patient sharing is performed on a patient or even more granular basis. Examples of further granularity include type of data such as labs, meds, can share data with each other on an as needed basis this is similar in concept to sending a fax containing medical information for a given patient from one organization to another. The receiving party (organization or healthcare provider 442), health organization/payers 448 in FIG. 4, can accept the sharing (similar to filing the received data into an existing or new patient chart) or reject the sharing request. In this manner, patient care teams are created in an ad hoc distributed way based on care requirements for each particular patient. In embodiments where security is a concern, the sharing is only performed between verified organizations (where verification is provided by peer organizations), is auditable by organization administrators and by the patients themselves. Patients also advantageously have the option to add/remove members from their care teams which can also include their relatives, PHRs, and digital devices and applications that generate, monitor, or consume healthcare data (PC2).

The collection of medical records in the standard and ad hoc forms is made possible by the parser 422, the uploader 420, and the parser 418 of the MINE 112. The document parser 418 parses the ad hoc data and whenever possible intelligently categorizes elements of the ad hoc data into structured elements. In some embodiments, natural language processing, neural network, user assisted templates, and other techniques are employed to intelligently categorize these elements. Intelligent categorization is the process of taking a segment of input text and assigning data category and structure based on the data category probabilistically to the segment of text. For example, the text "a1c was reported abnormal"—would be assigned the category "lab result" to the term "a1c" and associate the term abnormal as the result flag to the term "a1c" with some probability. Another example could be "stress test reported no cardiac malfunction" would associate the categories "problem" for the term "stress" and "cardiac malfunction", and the category "procedure" for the term "stress test". It would also associate negation to the term "cardiac malfunction". The document parser 418 then optionally presents the user with its analysis of the potential structured data for review and editing, through the output 117. The document parser 418 creates a standard XML document such as CCD or CCR formats that can be uploaded to the rest of MINE 112 through doc uploader 420. The document parser 418 also can provide users with a graphics user interface (GUI) that will allow them to easily map/identify structured elements in specific types of ad hoc documents to simplify the repeat processing of such documents. For an example, a user could bring up a document on the document parser and highlight the tag PatID: and indicate that the patient ID will follow this tag.

In some embodiments, the document uploader 420 is a computer program that is executed in any security domain. These security domains can be cloud based services, a hospital, a clinic, a personal computer and other suitable forum. The document uploader 420 receives standard XML documents such as CCD or CCR, from the parser 418 or directly from the medical sources 114, and uses this information to verify user information, and securely (usually via SSL) uploads the document to a desired destination within the MINE 112. MINE 112 maintains two main public environments (a product demonstration environment and a production environment) and multiple engineering environments. The type of document uploader employed is optional and a design choice. For example, the particular document uploader 420 employed in the MINE 112 depends upon the connectivity required. Documents can be sent to the document uploader 420 via a variety of methods including but not limited to IHE protocols, web services, shared folders, and drag-n-drop browser interfaces.

In some embodiment, the standard parser 422 is a computer program that is typically executed in a device in the Internet cloud but can, in other embodiments, be executed within a private network environment. The standard parser 422 parses and categorizes standard elements from the XML and creates data objects for specific standard elements. Most uncategorized data is stored as plain text into an ad hoc document object.

Additionally, the document parser 418 and the standard parser 422 advantageously identify and remove duplicate patients as well as duplicate documents. Identification of duplicate patients is done by comparing patient identification, as received by parser 418, from the source 122, to known patients with the MINE 112 and a determination of a threshold number of matches of the patient's received identification. For example, a patient whose social security matches a known patient record within the MINE 112 may be determined to be the same patient or a patient whose last name partially matches another last name and has other matching information, may be declared a duplicate patient. Patients can be matched based on similarities between demographic, clinical, billing, or any other relevant patient records within MINE 112.

The medical knowledge extractor 416 saves medical terms 410 (medical dictionaries, medical ontologies), medical knowledge 412, in digital formats, and medical knowledge gathered from the mapped data objects 434. The medical knowledge extractor 416 creates relationships between different medical concepts found in the medical knowledge. These relationships are stored in a series tables called relevancy matrix 426.

The relevancy matrix 426 are a set of granular tables of medical terms, their synonyms, additional search terms that are of interest and a set of multidimensional relationships that indicate the relevancy of each of the terms (apixions or events) to other terms (apixion/event) along various dimensions such as "lab for", "cures", "has reported negative interaction" etc. . . . , to medical professionals. The elements in the columns and rows of these tables are called "apixions" or alternatively "events", also referred to herein as "atomic healthcare related terms". As is appreciated, the set of granular tables grows over time as additional medical terms are identified by the MINE 112.

The relevancy matrix 426 includes tables that are organized at various information levels including but not limited to global information, specialty specific information, standards organization specific information, user specific information, disease or problem specific information, and patient specific information. Advantageously, users selectively and independently adjust their versions of the apixion table by performing a search and then adding or removing elements that they feel are relevant or not relevant to the intent of the search they conducted. The relevancy matrix 426 can process, aggregate, and propagate these user inputs to the other information levels.

The mapper 424 receives the structured and ad hoc medical information and the type (e.g., medicine, allergy, labs, notes . . . ) of information, from the parser 422, and uses the relevancy matrix 426 to generate mapped data objects 434 that include the medical information, the type of medical information and granular terms to which they are related (i.e., the related apixions). Apixions can be used to help identify the same data instances from different sources for reconciliation purposes and to identify similar data instances for comparison purposes. The mapper 424 also consists of a set of flexible rules that can be used to identify exact matches of data instances and "close" matches of data instances. The mapper 424 also records the result of these rules in the mapped data objects 434. Exact matches can be defined as mapped data objects 434 that are identical in the defined fields of interest. Close matches can be defined as mapped data objects 434 that meet some matching threshold on the fields of interest.

The search module 432 is analogous to the search module of the module 232 of FIG. 2 and receives the mapped data objects 434, the relevancy matrix 426 and search input from the user to generate lists of items for each type of medical information. Federated (cached or real-time retrieved data from multiple sources) data is assembled at run time to create a unified view of the patient's clinical history via a set of mappings or rules. Data from multiple sources are either collected in real-time via standards or proprietary query mechanisms or are retrieved from a previously indexed cache of such data. The data from these multiple sources are then combined for a single unified view. What is shown in the unified view depends on and is formed by the data mapper 424 (via de-duplication rules and the data mappings rules) and visualizer 438 which handles the organization rules, rights and privacy rules and the user's role. The search module 432 also ranks the list of items based on their relevancy to various factors such as the user input, a query, relevancy matrix, past user behavior, user role, privacy settings of the patient data, or knowledge gained from history of medical information. These results are passed onto both the visualizer 438 and the API 430.

To summarize, the data from multiple sources is indexed and meta-tagged by the data mapper 424. This data set is then consumed by the visualizer 438. The visualizer presents the same data differently to different end users (or output 117) based on who the user is and what role the user plays in the healthcare spectrum.

In FIG. 4, the API 430, the document uploader 420, and the ad hoc document parser 418 are included in the interface 113 of FIG. 2. The medical terms 410, the medical knowledge 412, the search 432, the visualizer 438, the mapped objects block 434, the mapper 424, the relevancy matrix 426, the medical knowledge extractor 416, and the business intelligence block 436 are a part of the processor 115, and the medical terms 410, the medical knowledge 412, the medical knowledge extractor 416, the visualizer 438, the mapped data objects 434, the mapper 424, the relevancy matrix 426, the standard parser 422, the ad hoc document parser 418, and the template library manager 428 are a part of the processor 116, and the HIE 122, the EMR 120, the HC provider 442, the patient 440, and the health orgs/payers 448 are a part of the outputs 117.

Document and medical data object search ranking is now described. To make medical data objects 434 matching search conditions (Search results 505) even more relevant, MINE makes use of a mathematical concept we call Concept Proximity Model (CPM). The CPM algorithm returns a numerical value indicating the relevancy between a pair of documents or medical data objects 434, or between a medical concept and a medical data object 434. The relevancy value can be expressed in various fashions including but not limited to as an Euclidian distance between two points in a multi-dimensional space, or in angular distance, from −1 to 1, indicating the cosine of the angle separating two vectors with the same dimensions.

To illustrate the use of CPM in relevancy ranking, the following is an example of how a relevancy metric is computed and retuned by CPM that can then be used as part of the search strategy. For any given document CPM calculates a numeric address based on the medical terms (Apixions) in the Relevancy Matrix 426. The numerical address, which can be expressed as a string of numbers or the coordinates of a point in a multi-dimensional space, can be calculated based on various attributes of the medical data in each document (e.g., presence of conditions, symptoms, abnormal labs, etc.) as they relate to Apixions. For instance, let us assume there are only the following three Apixions provided to CPM: medical conditions A, B and C. If a search string inputted by the user is semantically related to conditions A and C, the search criteria can be expressed as a vector, S=[1, 0, 1]. A document that indicates a patient diagnosed with conditions B can be expressed at a vector, D1=[0, 1, 0]. A second document that indicates a patient diagnosed with condition A can be expressed at a vector, D2=[1, 0, 0]. The angular distance, AD, between each document pair can be expressed as a normalized dot product between each vector pairs. In case of the above three vectors, the angular distance between vectors S and D1, would be greater than the angular distance between vectors D1 and D2. This ranking strategy suggests that in case of the above search criteria, document 2 should receive higher ranking and hence be listed closer to the top of the list of search results, than document 1. This ranking is particularly useful in cases where the keyword search indicates that condition A is found in both documents, but is mentioned in document 1 in a way that rules out the condition, as opposed to document 2, that indicates the diagnosis of the condition has been established. In this case, a search strategy using only keywords may not accurately establish the relevance of each document to the search term and may list document 1 above document 2. A simple example would be a document for a healthy patient explicitly listing negatives for each condition (e.g., "no chest pain", "no fever"), which would be incorrectly presented as being more relevant to these conditions than a document in which they are diagnosed positively for a condition.

For any given patient or document MINE can calculate a numeric address based on the medical terms (Apixions) in the Relevancy Matrix 426. The numerical address, which can be expressed as a string of numbers or the coordinates of a point in a multi-dimensional space, can be calculated based on various attributes of the medical data (e.g. presence of conditions, symptoms, abnormal labs, etc.) as they relate to Apixions. For instance, let us assume MINE has only the following three Apixions: medical conditions A, B and C. A patient record, R1, indicating that the patient has been diagnosed to have condition A and C can be expressed as a vector, [1, 0, 1]. Another patient record, R2, that indicates a patient diagnosed with conditions B and C can be expressed at a vector, [0, 1, 1]. If we assume that 1) the patient records are comprehensive, 2) all three medical conditions A, B and C to have been accurately diagnosed, and 3) the conditions are chronic, then a system comparing the two vectors can conclude with a certain level of certainty that patient records, R1 and R2 do not belong to the same patient, even though the patients may share the same name.

Such a numerical address has a certain level of uniqueness for patients with a fair amount of data points particularly if the patient's record contains many data points that deviate from the norm (healthy) and therefore can be used as a parameter in addition to the patient's ID in order to establish a unique patient identification. The same strategy can potentially be applied to reconciling duplicate documents and data points.

Community-based template review, approval and sharing system is now described. As described above the template lib manager 428 and the visualizer 438 control the display, position, size and behavior of widgets based on pre-defined default and also user-customizable settings. Once an optimal display configuration has been reached, the desired configuration (referred to as a "Template") settings can be submitted to an online community for them to review, test and if desired, rate or even certify the Template. The profiles of the online community and their Template submissions can either be kept private or made public via configurable privacy settings. All users within a community network would have access to the submitted Templates and can test, write reviews or rate the published templates. A decision body or board within a given user network has the ability to certify a Template, making it visible to all users within the community that the Template has received certification. Certification description can have many attributes including date, name of the certification body and other pertinent information.

The capability of "Did You Know?" is now explained. The system searches the history of the patient and displays information that may indicate significant risk for the patient or may have a significant influence on the diagnostic process or treatment plan, based on the patient's "current circumstances". A patient's "current circumstances" includes the patient's current problems, medications, allergies, available measured information (labs, diagnostics, etc.) and any active complaints or symptoms they may have. For example, a patient who is complaining of sore throat and fever might have past splenectomy information displayed by the "Did You Know?" feature, since there is a relation between these circumstances and a serious complication due to past splenectomy.

II. Query Processes

The MINE 112 may employ finite state transducer technology to identify a medical concept in a health record, and is able to suggest possible completions. The MINE 112 uses its Semantic Query Processing Engine capable of understanding medical language to tag medical concepts in the query. Using such tagged information, MINE 112 is able to search both the textual content and structured information present in the patient's history by using MATRIX 414 (Medical Application Terminology Relation IndeX), a proprietary knowledge base of medical concepts and the semantic relations between them. Note that MATRIX 414 can be external or internal with respect to MINE 112, or combinations thereof.

For example, in the query "chest pain with palpitations", the terms "chest pain" and "palpitations" are automatically tagged with concepts from MATRIX 414.

In some embodiments, MATRIX 414 knowledge base can include approximately four or more million primary medical concepts and tens of millions of relationships between the concepts. This extensive knowledge base can be constructed by a combination of various techniques. For example, many of the commonly used clinical terminologies like ICD-9, CPT, and LOINC have been integrated into MATRIX 414. Further, content from a variety of large medical corpora like medical references and text from medical encounters is processed extract medical knowledge. Additional concepts, abbreviations and synonyms are identified in this way. NLP technologies such as named entity recognition (NER) are used to recognize various medically relevant concepts within the text. This processed text is passed through a Statistical Semantic Analysis Engine ENGINEREF which has been optimized to predict the strength of relationship between two medical concepts. This combination of pre-existing terminologies and new relationships mined from medical corpora creates a knowledge base that drives a Search Engine of MINE 112 to return the most relevant structured data and unstructured content in response to any free text query.

The deep integration of MINE 112 with the MATRIX 414 knowledge base filters out irrelevant structured data—and presents a care provider with the information most relevant to his needs. In one example, the searcher will see that unrelated problems are filtered out—and only the problems that might be related to the complaint are highlighted. Because of the MATRIX 414 knowledge base, MINE 112 is able to highlight "shoulder pain" when the searcher is querying "chest pain" because it is strongly related to chest pain. MINE 112 is also able to perform similar highlighting for lab tests and procedures.

Apart from providing sophisticated concept based search on structured data, MINE 112 uses state of the art indexing and search technologies to provide semantic searching capabilities for textual content found in encounter notes. MINE 112 understands medical concepts and knows to search for "chest pain", and also for its synonyms such as "chest pressure" and "chest discomfort". MINE 112 can display easy-to-scan snippets for each medical concept found in the text, giving the health care provider immediate access to relevant information.

MINE 112 uses the knowledge available from existing medical terminologies and combines it with knowledge extracted using sophisticated semantic analysis techniques to provide health care providers the critical ability to access relevant information instantly at the point of care.

Figure 5:
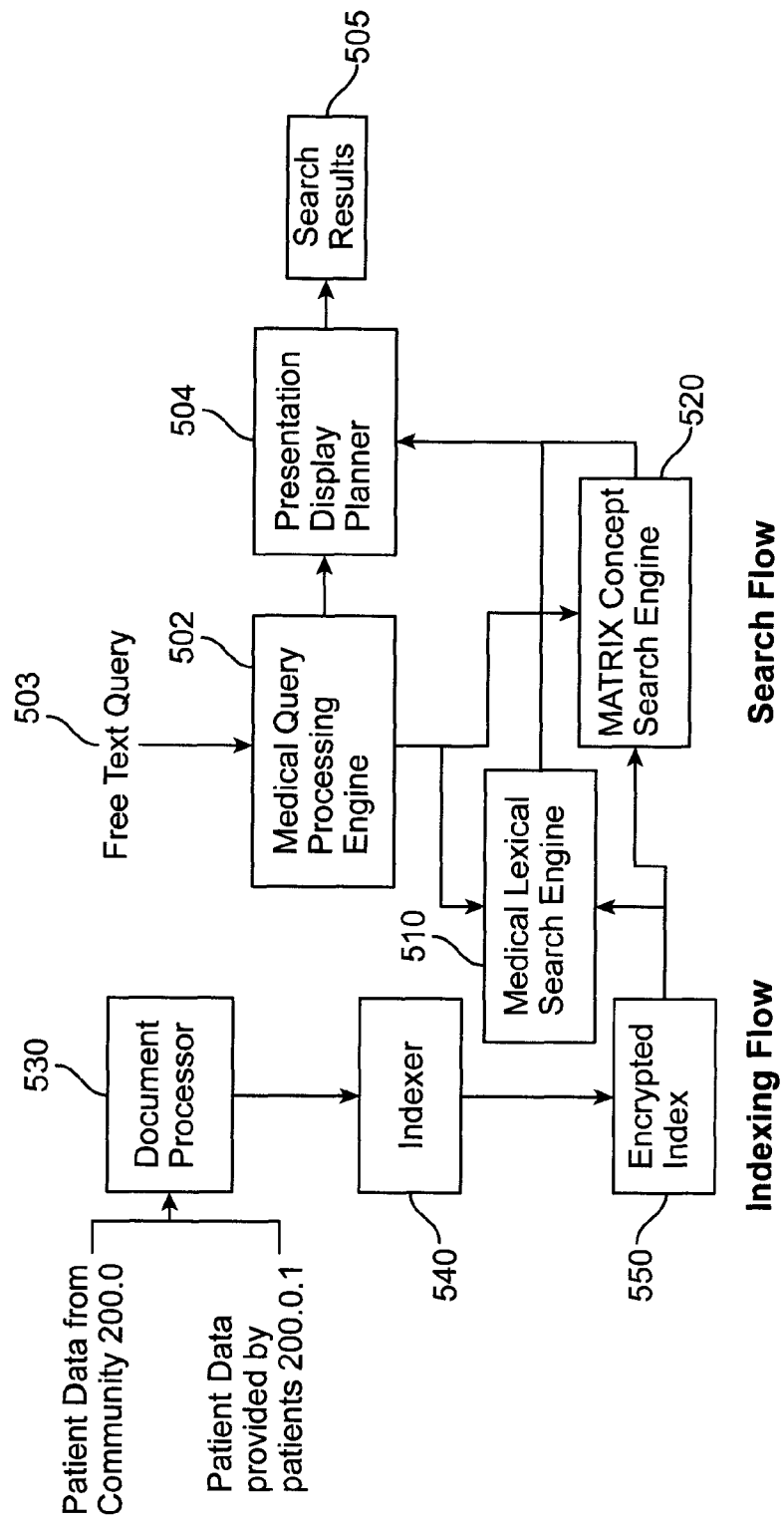
FIG. 5 shows a block diagram of the indexing, querying, and searching functions of the MINE 112, in accordance with some embodiments.

FIG. 5 shows a block diagram of the indexing, querying, and searching functions of the MINE 112, in accordance with a method of the invention. An indexer 540 is shown to receive documents from the document processor 530 and to provide indexed documents to the encrypted index module 550, to be encrypted. The medical query processing engine 502 receives a free text query 503 and processes the same and provides the processed query to the medical lexical search engine 510 and to the matrix concept search engine 520. The engines 510 and 520 also receive the encrypted document from the module 550 and provide a medical search engine output and a matrix search engine output, respectively, to the presentation display planner 504. The planner 504 ultimately provides search results 305 as its output. The engine 502 also provides output to the planner 504.

The document processor 530, indexer 540, and module 550 are generally located within the processor 116, in some embodiments. The engines 502, 510, and 520, and the planner 504 are located within the processor 115, in some embodiments.

The document processor 530 receives community patient data 200.0 and patient-provided patient data 200.0.1 for processing. The data 200.0 is provided from sources other than the patient whereas the data 200.0.1 is provided by the patient.

The engine 502 converts free form natural language queries, free text query 503, into calls to the engines 510 and 520. The engine 510 finds all objects having the keyword term match (perfect or loose) anywhere in the content of the medical data object, and filters them using other keywords. The engine 520, for a predetermined collection of medical terms, finds a list of medically related terms, identified through a knowledge base comprising medical terms, semantic relations, and strength of the relations. The collection of medical terms is dynamically changing according to user-input and otherwise, as the system 100 gains medical knowledge. The planner 504 converts the output of the engines 510 and 520 into a unified display plan for viewing by a user and this becomes the search results 505—medical data objects that can be matched to either keyword or concepts.

Two data flows are shown in FIG. 5. Indexing flow follows the flow of data from the 200.0 and/or 200.0.1 to the processor 530, the indexer 540, and the module 550, to the engines 510 and 520. Search flow follows the flow of data from receipt of the query 503 to the engine 502 to the engines 510 and 520 to the planner 504 to generate the search results 505.

In the search flow, the engines 502, 510, and 520 are used to process documents and convert them into formats that make them easy to quickly search and retrieve from a large collection of documents. The indexing flow allows for reliable and automatic replication of documents across multiple physical machines. Indexing also supports large throughput (large number of documents getting indexed per minute) because it can split the work load over a large number of machines, such as multiple processors. The indexer 540 converts the incoming healthcare data into a form that makes the querying faster. The indexer 540 also stores the contents of the data in a completely encrypted format so that in case of data theft, the protected health information (PHI) is not revealed.

The module 550 stores patient data, which it receives from the indexer 540, in the form of an indexed document, in an deidentified format that is also easily searchable and generates deidentified indices. There may be multiple deidentified indexes to allow for rapid searches for different kinds of queries. The Protected Health Information (PHI) removed may comport to HIPAA definitions of PHI, including names, dates, particular results, addresses, etc. This deidentification protects patient data from data theft, and supports compliance with HIPAA. In alternative embodiments, the deidentified indices, generated by the module 550, may be stored in multiple processors and queried independently—thus they are fault tolerant and protect PHI. The deidentified indices enable very high performance searching of records without having to decrypt previously encrypted data. Once the target population has been identified, then the PHI can be decrypted efficiently to reintegrate the PHI with the clinical data.

As described previously relative to FIG. 5, the search engine consists of two distinct components—namely the indexing flow and the search flow. The indexing flow consumes patient data from the community (in multiple formats including CDA templates, CCR, CCD, PDF, images, etc.) as well as data provided by the patients themselves. Patient-provided data can come in the form of patient uploaded material such as status updates or images, videos and documents or can be from health monitoring devices connected to the internet. The indexing flow processes each of the documents received by the system and converts them into structures that make the searching of this data efficient (Indexer 200.2). These structures are stored in a completely encrypted fashion to protect patient information.

The search flow takes as input a free text query (i.e., a query without any restrictions on the structure)—and converts the free text query into commands to the Medical Lexical Search Engine and the MATRIX (Medical Application Terminology Relationship IndeX) Concept Search Engine using a sophisticated query processing engine optimized to work with medical queries. The results of the search engine are sent to the presentation display planner (504)—which decides the most relevant presentation given the users role and privileges and their organizations roles and privileges (e.g. provider, administrator, quality manager, and the patient) and the search query.

Figure 6:
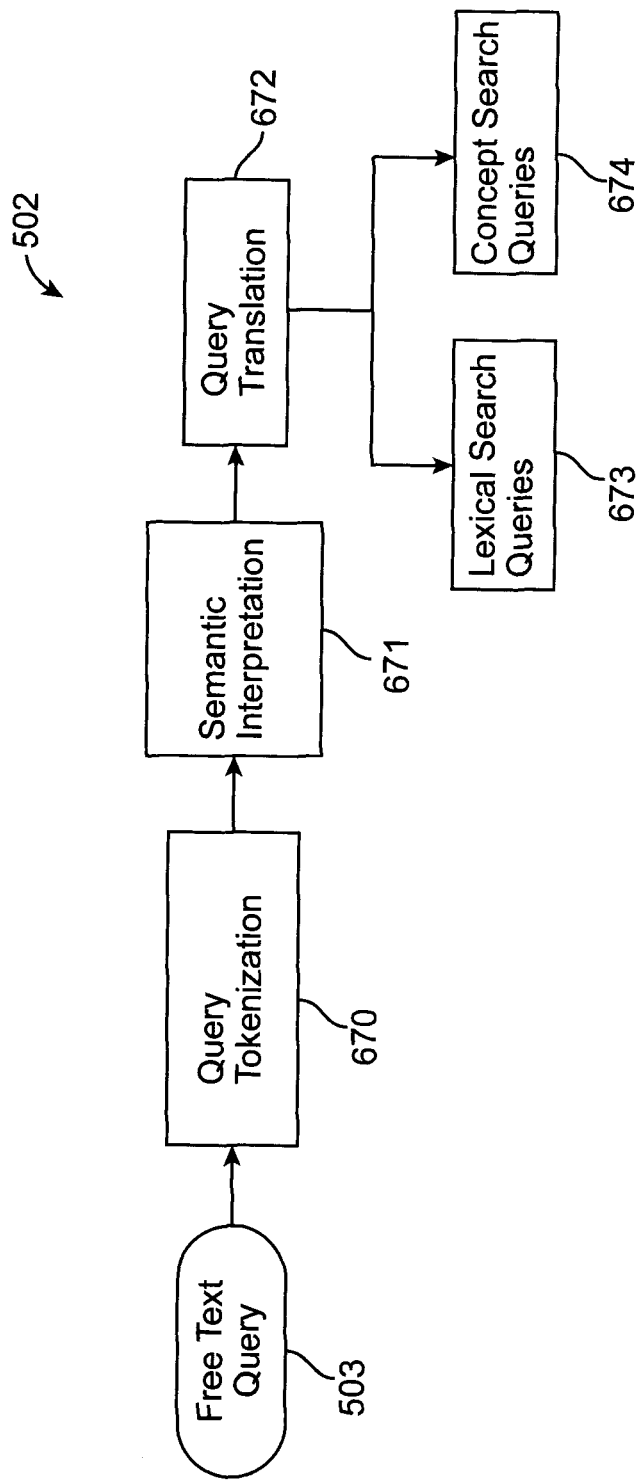
FIG. 6 shows an example block diagram of the query module, in accordance with some embodiments.

FIG. 6 shows a block diagram of the medical query processing engine 502, in accordance with some embodiments.

The query module 502, also referred to herein as "medical query processing engine", is a part of the module 232 of FIG. 2 and is shown to have the free text query 503 received by the query tokenization module 670, which is shown to provide tokenized query to the semantic interpretation block 671, which, in turn, provides interpreted semantic results to the query translation block 672. The block 672 provides query translation to the lexical search queries block 673 and the concept search queries block 674. The engine 502 converts free form natural language queries, or the free text query 503, into input that can be used by the engines 510 and 520 by first tokenizing the query 503, performed by the block 670, using a large dictionary of medical terms to identify all possible interpretations of the terms in the query. An interpretation for a query consists of all the medical terms that were found in the query along with their medical types. Thus, tokenizing a query, in some embodiments, uses a dictionary of medical terms to identify all possible interpretations of the terms in the query. It also consists of any relation that can be recognized between the medical terms in the query based on function words such as "with" and "of".

Each interpretation is scored based on the surrounding context, for example, other words, medical terms and relations present in the query, or the knowledge provided by the application to the query processor such as the history of previous queries and user responses. After scoring all interpretations that are generated, the interpretation with the highest score is chosen as the most likely interpretation of the query. The most likely interpretation of the query is translated into a lexical search query 673 and a concept search query 674 and sent to the lexical search engine 510 and the concept search engine 520.

The most likely interpretation is then transformed into calls to the engines 673 and 674 for lexical and concept search, respectively. Once the results are returned from the searches the query processing engine annotates the returned results with information about the query so that it can send it to the display planner to create an appropriate display plan.

Figure 7:
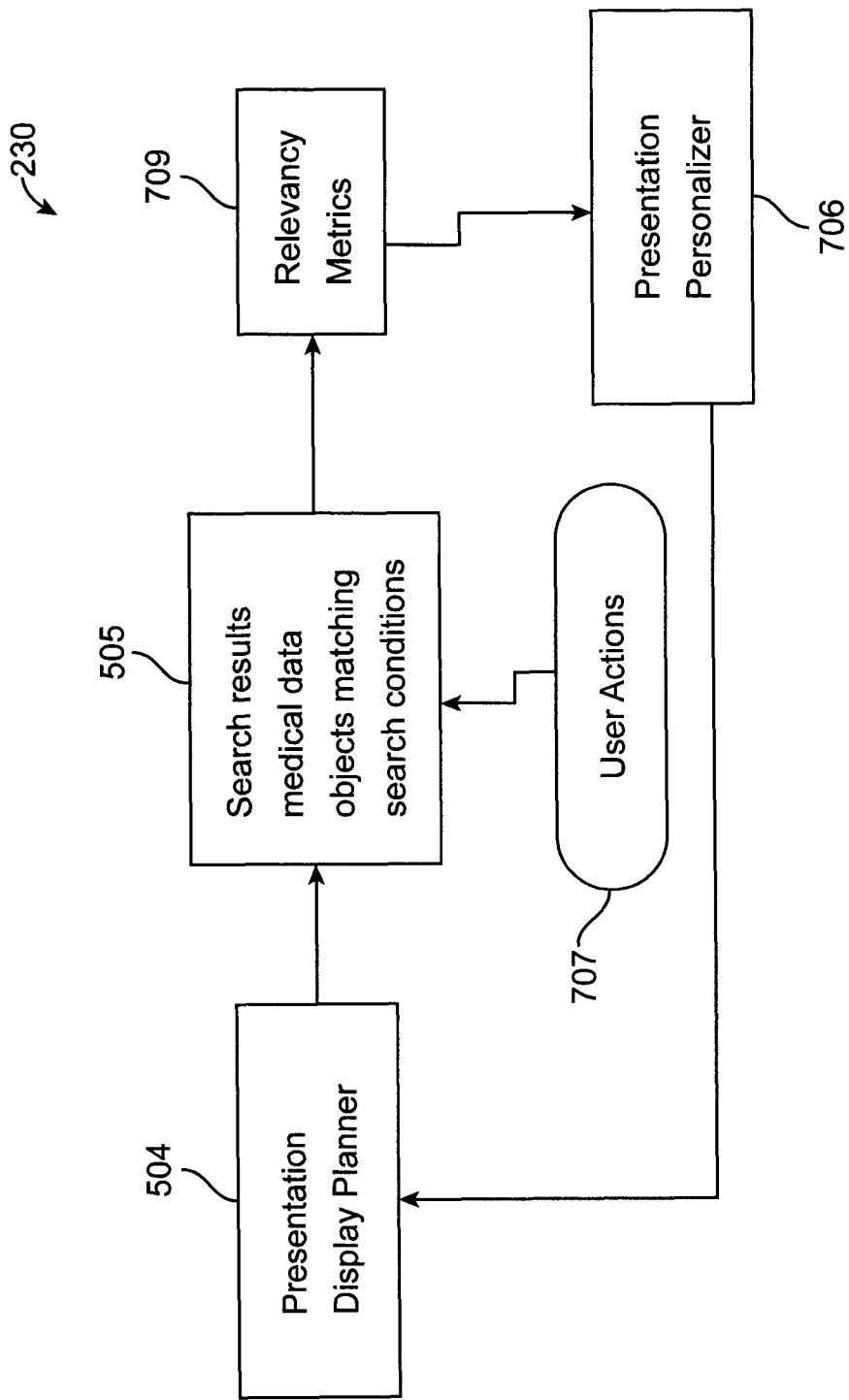
FIG. 7 shows an example block diagram of the relevant blocks/functions of the presentation module of the module 230 of FIG. 2, in accordance with some embodiments.

FIG. 7 shows a block diagram of the relevant blocks/functions of the presentation module of the module 230 of FIG. 2. A presentation display planner 504 is shown to receive input from a presentation personalizer 706 and to provide search results 505 that are in the form of medical data objects matching search conditions. The search results 505 receives user actions 707 and serves as input to the relevancy metrics block 7309, which is shown to provide input to the presentation personalizer 706.

The planner 504 receives, as input the annotated results for a query, from the personalizer 306, and converts them into an ordered (ranked) list of results to be presented to a user. The ranking component includes exhaustive medical knowledge available in MATRIX to decide the relevance of data objects. Each result can be different in its presentation. The planner 706 also records user actions 707 on the output of the search results such as user clicks and dwell times. This information is logged internally for computing relevancy metrics and to provide personalization. For example, a result containing laboratory results can be displayed as a trend line over time whereas results containing problems can be displayed with special markers indicating the onset of the problems, related medications and procedures for the problem. A problem or condition that has been cured can be displayed differently from a present problem to indicate that the problem is no longer active. Apart from creating display plans for each result, determining its styling, content, and presentation (for example, graph vs. highlighted text) the display planner also determines the global order of results. For certain types of queries (for example, queries about analytes and lab tests) certain types of results might be prioritized over others.

The planner 504 uses logged relevancy metrics along with user data to personalize the presentation for the user and the query. On every query and user this data is captured and stored. The personalizer 706 may periodically analyze the relevancy metrics captured for each user and query and converts them internally to a personalization model which is applied when presenting the search results to the user at query time. This process creates a feedback loop increasing the relevancy of results returned for each user.

Figure 8:
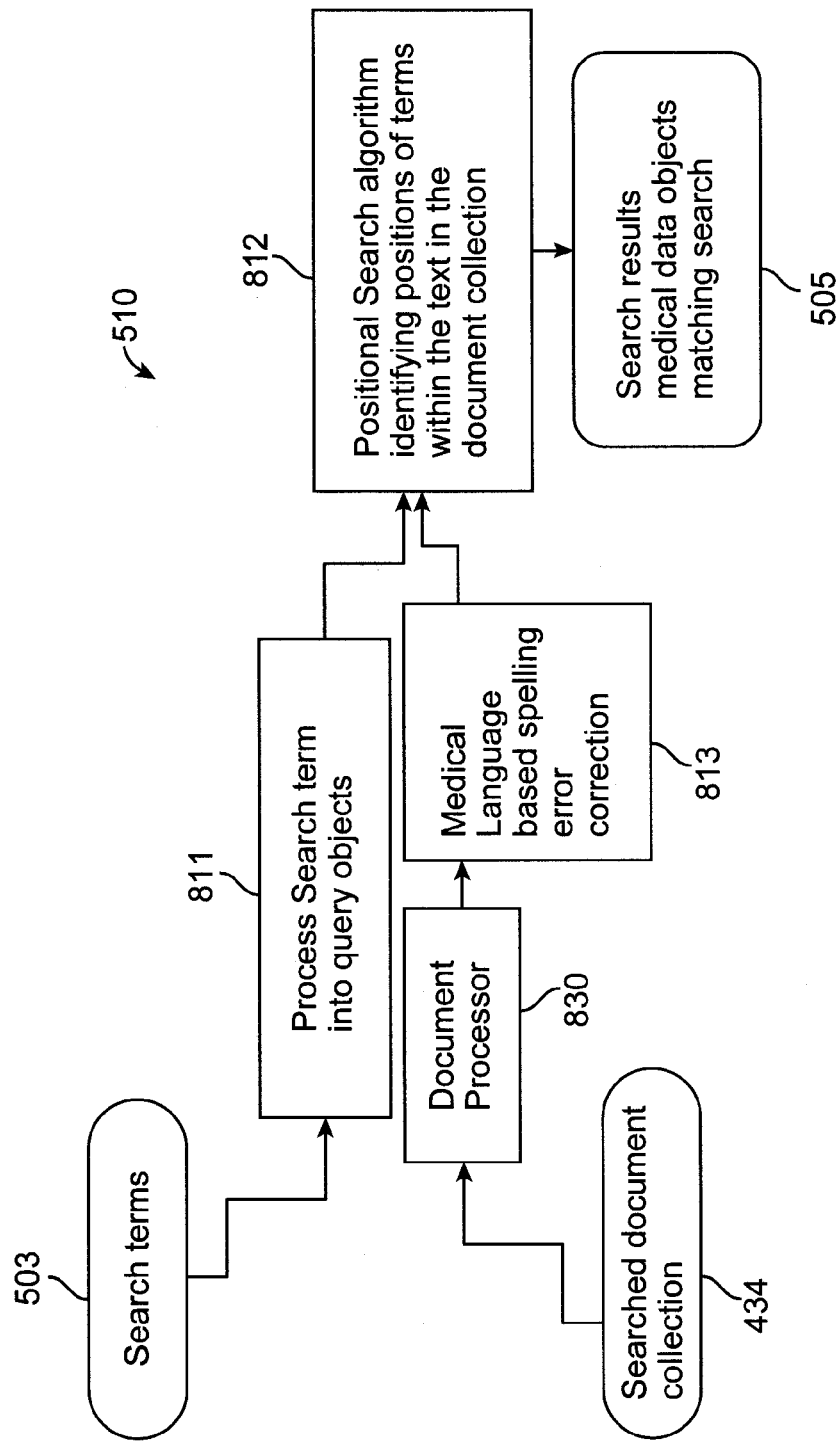
FIG. 8 shows further details of the medical lexical search engine 510, in accordance with some embodiments.

FIG. 8 shows further details of the engine 510, in accordance with an embodiment and method of the invention. The search terms 503 and the search document collection 434 are received, the former by the process search term into query objects block 811, and the latter by the document processor 330. The processor 330 processes the searched document received from the collection 203 and sends the same to the medical language based spelling error correction 813, which corrects misspellings and sends the corrected text to the Positional Search algorithm 812 for identification of positions of terms within the text in the document collection, with the final search results 505 of medical data objects matching the search. The search terms 503 is received by the block 811, which processes the search term into a query object.

Figure 9:
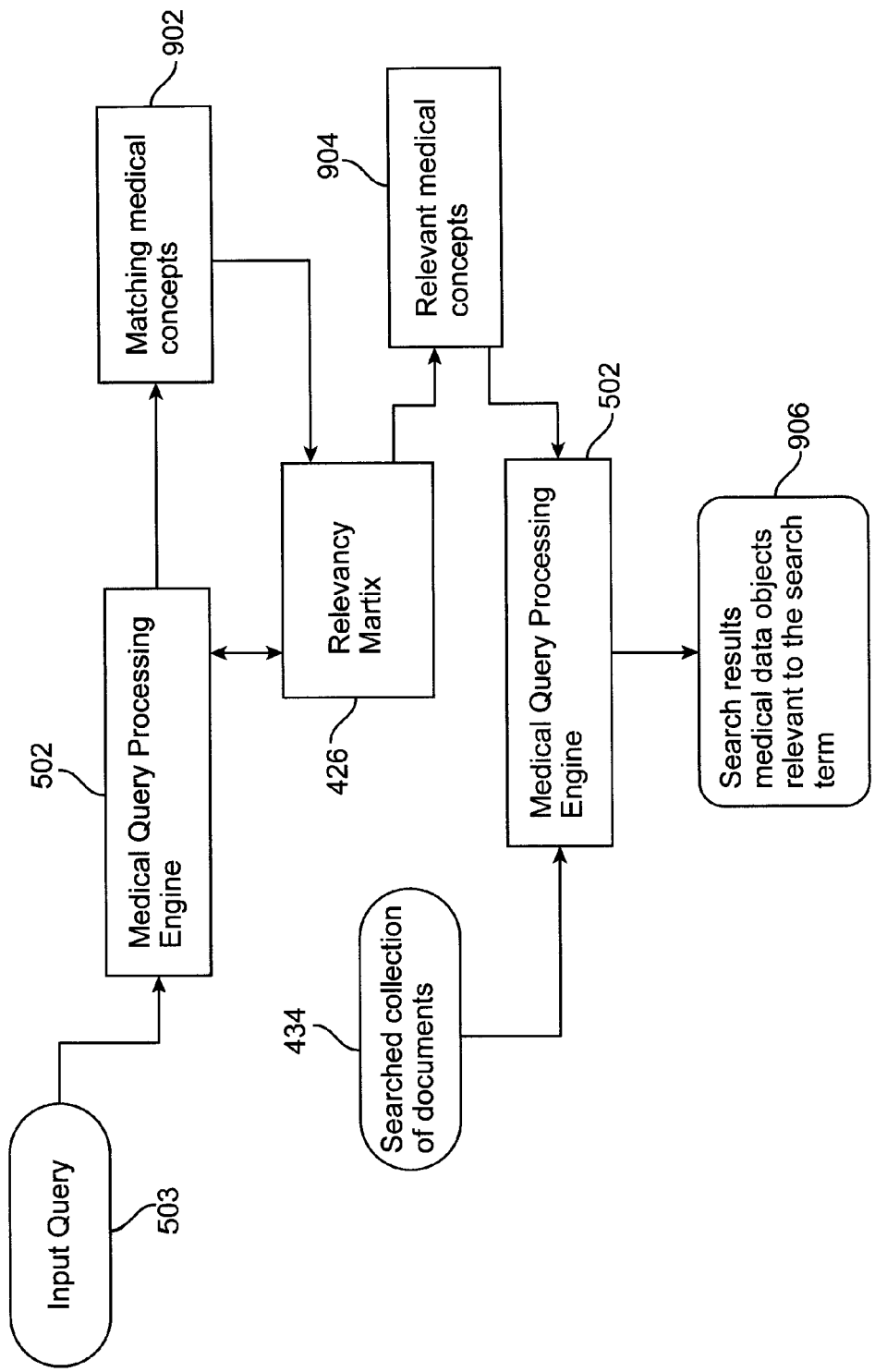
FIG. 9 shows further details of the MATRIX concept search engine 520 of FIG. 5, in accordance with some embodiments.

FIG. 9 shows further details of the engine 502 of FIG. 5, in accordance with some embodiments. The input query 503 is received by the medical query processing engine 502, which processes the received query using the relevancy matrix 426 and outputs from the processed query a set of matching medical concepts block 902. The relevancy matrix 426 uses the matching medical concepts block 902 and filters it to generate only the relevant medical concepts (block 904). The relevant medical concepts block 904 obtained as the output received from the matrix 426 is fed back to the medical query processing engine 502. The engine 502 further receives searched collection of documents 434, which in combination with the relevant medical concepts block 902, is used to generate search results 906. The search results 906 include medical data objects relevant to the search term, as previously discussed.

The engine 502 is knowledge-based and includes a table of medical terms, concepts, relational links between concepts and numeric values (relevancy scores) providing a quantitative measure of the strength of the relational links. This collection of numeric values is referred to herein as the relevancy matrix 426. The normalized relevancy score has a range between 0 and 1, with 0 being completely unrelated (orthogonal) and 1 been highly related (e.g. synonymous). It is noted that in other embodiments, the opposite or a different range may be employed, for example, 1 may be used to reference unrelated and 0 may denote highly related. The relevancy scores are obtained through a collection of machine-learning algorithms that operate over collections of data obtained by a variety of sources, including, but not limited to, data generated by experts and medical practitioners including clinical data stored within the system, data obtained from usage statistics and data obtained by converting publicly available medical texts into knowledge usable within the matrix.

In order to identify all the concepts relevant to the search term, the knowledge base is queried with the search term to find all the concepts that are related to the search term. When all the matching concepts are found the relevant items can be selected by filtering the list of returned concepts based on their relevancy score. The threshold for filtering is a relevancy search parameter that determines the stringency of the algorithm, from selecting only synonyms to finding all remotely related concepts.

The identified list of relevant medical concepts is passed as an input to the medical query processing engine which is then able to generate relevant lexical queries for the lexical search engine 510 to return the search results 906.

An additional level of complexity in identifying relations between medical terms is created by negative semantic constructs. For example, occurrence of the words "diabetes ruled out" in the context of a medical document needs to be interpreted by the relevancy engine as a negative relevancy value for diabetes. From the semantic algorithm perspective, two main problems associated with negations are detection and interpretation. Negation detection algorithm relies on the collection of negative semantic constructs found in the medical texts and falling into several categories, from simple negation, like "no fever", to more complex patterns like "no sufficient evidence of infection". The negation detection algorithm uses a machine learning model to learn structural patterns in sentences to identify if the phrases in the sentence are negated or not.

Interpretation of negative relevance values depends on the specific use case. When application requires only detection of relations between concepts with no discrimination for their type, negative relevancy values can be used as absolute values. However, building decision support elements requires understanding of the semantic interactions between medical data objects, so interpretation of negative relevancy values becomes critical.

III. Population Data Analysis

As previously noted, the MINE 112 enables population wide data analysis. Healthcare reform has brought about initiatives such as accountable care, sustainable health and shared savings. Participating organizations are challenged to decrease cost of care, measure population health, improve quality and demonstrate meaningful use. To comply, they need to effectively leverage ALL their data whether that information exists within provider offices, acute care settings, or billing systems. Using data is further challenged since approximately two-thirds or more of the key clinical information is typically found in free text notes and scanned documents, which are inaccessible and unusable by today's healthcare technology solutions.

Healthcare organizations can use MINE 112 as their data foundation to aggregate and unlock the full potential of their coded and unstructured data from across multiple sites. Clinical Knowledge Exchange (CKX) CKXREF approaches healthcare information exchange (HIE) with AI-based processing. Typically, an HIE needs to go beyond exchange of standard data to deliver actionable information. Accordingly, the CKX CKXREF Data Interface 113 is capable of importing data in many formats. Further, MINE 112 can include a Reconciliation and Deduplication Module for reconciling the imported data, and MINE 112 can also include an Indexing and Meta Tagging Module for tagging the imported data in a manner that makes the information ready for viewing and analysis. Hence, MINE 112 permits the use of coded data such as template entries and claims data, and also makes useful unstructured data found in clinical narrative. If the clinical narrative is in scanned documents, CKX CKXREF automatically extracts the textual information using Optical Character Recognition (OCR). The post processed and original data can be stored in a High Performance Data Storage unit(s), locally or distributed, resulting in queryable and computable with sub-second response.

CKX CKXREF can also interoperate with EHRs, HIEs, PACS, Quality and Billing Systems. For example, MINE 112 can receive and process many types of data from EHRs and PMs including coded data, textual and image-based documents by leveraging a combination of proprietary and standard data interfaces. Standard data interfaces supported include CCD, CCR, C32, X.12 and HL7 V2. MINE 112 can also supports HL7 V2 and IHE XDS, IHE XDR protocols for hospital and enterprise level integration.

In addition, MINE 112 can also inter-operate with any application and bi-directionally exchange clinical information using the API APIREF.

Data Security and Privacy

Data Security and Privacy can also be integral to MINE 112. To ensure data security and privacy, MINE 112 applies best practice standards and technology in data encryption. For example, to ensure HIPAA compliance, MINE 112 limits clinical record access to only members of a patient's care team. Others not on the patient's care team, such as in case of urgent care providers, can gain immediate access to the patient record by "breaking the glass". These transactions can be tracked and be fully reportable.

A data exchange module which handles output 117 may transmit and receive data in using industry standard SSL connections and all Protected Health Information (PHI) may be encrypted. This module can also maintain detailed audit logs for all applications and users accessing data. The secure data access is optimized for web-browser viewing on most platforms including Windows, Macintosh, Unix, Linux, iPad, iPhone, Android, and Blackberry.

Data Consistency

Many patients, especially older individuals with many chronic diseases, seek care from by multiple healthcare providers working in separate and diverse environments, including private practices, group practices, and hospitals. Each of these sources generates data to describe and code the patient's medical information differently, and will eventually create a distinct continuity of care document for each encounter. The MINE 112 can analyze the patient's entire record, organize it, and present it to the healthcare provider in a format that can be efficiently viewed and interpreted. Reconciliation and de-duplication of data are performed dynamically by the Reconciliation & Deduplication Module for presentation using Presentation & Quality Checking Module, while data is also kept in its original form, without data loss.

Master Patient Index

MINE 112 can also include an Enterprise Master Patient Index technology (EMPI) EMPIREF. MINE 112 can use an existing EMPI or leverage IHE PIX/PDQ standard or operate independently. This EMPI can operate in two different modes: (1) Automatically find matching patients based on organization specific rules or (2) the Presentation & Quality Checking Module of MINE 112 enables users to identify potential matches and merge records on-demand. MINE 112 can keep track of all patient merges and allow users to un-merge records in case of an error. The Indexing & Meta Tagging Module of MINE 112 can also include fuzzy match algorithms that can be used for population analysis.

Application Programming Interface (API)

For software application vendors providing EHR, HIE, PHR, PACS, home monitoring, or medical devices, and those who are developing novel health applications, the system API APIREF offers the unique ability to exchange data with the Clinical Knowledge Exchange CKXREF platform using a SOAP API APIREF. The medically intelligent search solution can also be embedded inside an application using a REST API APIREF.

Examples of sections and vocabularies supported by MINE 112 include Problems (free text, ICD9 codes), Office Notes (full, adhoc text in CCD), Medications (free text, RxNorm codes), Allergies (free text), Labs (free text, CPT codes), Procedures (free text), and Immunizations (free text).

In some embodiments, the MINE 112 system may also interoperate many other systems, including EHRs, HIEs, PACS, Quality and Billing Systems.

Population Analyzer

In some embodiments, MINE 112 also includes a Population Analyzer that provides an on-demand and flexible solution for clinicians, care managers, and administrators to efficiently manage a group of patients and better target interventions to achieve better care experiences and population health improvement. This tool is an essential dashboard to help guide a performance-driven organization to meet clinical and financial objectives.

Using the latest advances in big data science, the MINE Population Analyzer can provide in real-time very accurate views of a patient population at multiple levels, including but not limited to:

a. disease and condition registries
b. patient risk stratification (e.g., co-morbidities)
c. quality measure compliance (e.g., Medicare PQRS and ACO measures)
d. patient-level actionable care gaps (e.g., diabetics who need retinal eye exams)
e. clinical questions answered using intelligent population search The MINE Population Analyzer can intelligently mine and extract relevant data from the clinical narrative to enrich existing coded data, all of which may be aggregated from multiple data sources. This greatly improves condition identification, measure reporting, risk assessment and other clinical analyses. The Population Analyzer results can be viewed according to the type of data used in the analysis: coded data only versus coded data plus information mined from textual data. With Population Analyzer, there is no need to create custom, costly, and time-intensive reporting views or cubes.

The MINE Population Analyzer may be directly accessed within many clinical management platforms or electronic records via MINE 112 application interface 113 and an interface for the output 117. Furthermore, the data and results can be queried by quality reporting and decision support systems.

The MINE population analyzer enables the user to request (via text query, API call, GUI, and other interfaces) aggregated statistical information for a specific cohort of patients, computed from structured data only AND computed from a combination of structured and unstructured data.

Such information includes, but is not limited to, #males, #females, #diabetics, #(other conditions of interest), numerator, denominator and %compliance for specific measures of interest (e.g., PQRS, CORE, ACO 33, HEDIS, etc.)

A cohort can be any set of patients. Some cohorts of specific interest are patients enrolled in an ACO or other care management organization, patients seen within an organization, patients seen by a particular provider, patients seen by a particular specialty within an organization, patients covered by a particular health plan, insurance or plan type. Many other cohorts can also be of interest.

Any group of patients that comprise a result value in a page of results (e.g., organization results, provider results, etc.) is a "Result Cohort." The minimum cohort displays will be by organization and by provider.

MINE Population Analyzer can also enable the user to "drill down" to a page of specific results for each patient in a cohort or result set. Patient-level results shall include results (facts) for specific clinical measures (e.g., PQRS, CORE, HEDIS, ACO 33, etc.), and specific documents and information sources that were used to infer results or facts about the patient.

Accordingly, the MINE Population Analyzer may include one or more of the following capabilities:
  a) scalable system to process large amounts of data and store it into the patient model.
  b) The ability to quickly query across the data for known use-cases (e.g., query by problems, pairs of problems, etc.).
  c) A usable system that supports SQL like queries so non-technical users can use the system (select, project and aggregate functionality).
  d) Usable from Pig 0.9.2 (release version of this document, 0.10 is out, but it is not yet in "stable" branch).
  e) Both streaming/in-memory access to the data.
  f) AES compatible encryption can be supported from the Get-Go, no excuses.
  g) Pig 0.9.2 schema types (i.e., schema as enforced by pig).
  h) Blobs in the dataset can be represented as SortedSpillableDataBag with a tuple having the following chunk information (offset, chunkdata (upto 1 MB), checksum).
  i) Immutable column families (because alter table is a map-reduce job away).
  j) Metadata can be stored in the TFile metadata block.
  k) Writes can be lock-free and resort to anti-entropy mechanism (maybe lamport timestamps/vector clocks/version clocks).
  l) Replication, high-availability etc. can be handled by hadoop.
  m) Backups are distcp to s3 (no incremental backups, but we can have rolling backups, etc. but they are all cron jobs outside of the system).
  n) Each value tuple can have the following information:
     Row key (BYTEARRAY)
     Format Version (INTEGER)
     Version (LONG) (used in read-repair scenarios)
     Writer Timestamp (LONG)—(timestamp, as seen by the writer in_seconds_)
     Active (INTEGER) (0/1) value indicating if
     A sequence of values which is in-of-itself another tuple (TUPLE, matching the schema in the metadata block).
     Any blobs can be represented as a sorted spillable data-bag with an internal chunked encoding.
  o) The key it the tfile can be MD5 of the key itself
  p) The metadata block of the TFile can include an index over the keys (so we load the first metdata block and load data files from it).
  q) Since TFiles are immutable, "merge" or grim-reaper jobs can be required including performing read-repair.
  r) Realtime Reads can happen through a service that loads the metadata block into an in-memory array and indexes into the t-file (include random network reads, but good caching should make this problem relatively easier).
  s) Realtime writes happen by updating the metadata block and a corresponding commit log (which is a file that is written to hadoop and flushed immediately).

| Muir ACO, PQRS | | | |
|---|---|---|---|
| | | Males | Females |
| # of patients | xxx | xxx | xxx |
| | | Coded | Text + Coded |
| # of diabetics | | xxx | yyy |
| # of HF | | xxx | yyy |
| # of CAD | | xxx | yyy |
| # of COPD | | xxx | yyy |
| # of HTN | | xxx | yyy |

| | Coded data | | | Coded + Text | | |
|---|---|---|---|---|---|---|
| Measure | num | denom | % comp | num | denom | % comp |
| diabetes with retinal eye exam | 10 | 100 | 10% | 10 | 100 | 10% |
| diabetes with foot exam | 15 | 300 | 5% | 15 | 300 | 5% |
| HF with LV eval | 20 | 100 | 20% | 20 | 100 | 20% |

| Search Term: Dr Smith PQRS | | | |
|---|---|---|---|
| | | Males | Females |
| # of patients | xxx | xxx | xxx |
| | | Coded | Text + Coded |
| # of diabetics | | xxx | yyy |
| # of HF | | xxx | yyy |
| # of CAD | | xxx | yyy |
| # of COPD | | xxx | yyy |
| # of HTN | | xxx | yyy |

| | Coded data | | | Coded data + Text | | |
|---|---|---|---|---|---|---|
| Measure | num | denom | % comp | num | denom | % comp | Health System |
| diabetes with retinal eye exam | 1 | 5 | 20% | 1 | 5 | 20% | |
| diabetes with foot exam | 3 | 10 | 10% | 3 | 10 | 10% | |

| Search Term: John Sample PQRS | |
|---|---|
| Measure | Numerator |
| diabetes with retinal eye exam | NO |
| diabetes with foot exam | YES |
| HF with LV assessment | NO |

(click on the measure and get the set of measure facts)

| Measure | Measure Facts | Source | Date |
|---|---|---|---|
| diabetes with foot exam | Diabetes | Claims | Jan. 1, 2012 |
| diabetes with foot exam | Foot exam | Doc | Feb. 12, 2012 |
| diabetes with foot exam | Foot exam | Doc | Jan. 12, 2011 |
| diabetes with foot exam | Foot exam | Doc | Nov. 12, 2011 |
| diabetes with foot exam | PCOS | none | na |

Quality Optimizer QMREF

The analysis of care quality within any healthcare organization begins with understanding how well patients are being treated according to evidence-based care measures. These results become the basis for managing populations, targeting patient interventions, and profiling physician performance. It is difficult to manage what cannot be readily measured. For many organizations, the process of quality analysis can be time-consuming and costly and often inaccurate.

As discussed above, approximately two-thirds or more of the data useful for quality measure sets in common use (e.g., Medicare ACO, PQRS, and HEDIS) is typically found in free text notes and scanned documents. This narrative information cannot be easily processed by quality reporting tools in use today. In addition, the relevant data may be located in multiple systems across an organization. As a result, these tools may under-estimate performance or include ineligible patients into reporting and analysis, decreasing overall accuracy.

The MINE 112 can aggregate clinical and billing data from multiple systems within an organization. MINE 112 can intelligently mine both discrete and textual data in an automated fashion for relevant quality measure concepts. MINE 112 can apply terminology codes for relevant data found within the clinical narrative. MINE 112 can export information to most quality tools including GPRO using application interfaces 113 and 117. MINE 112 can expose a validation tool for clinicians and others to view source documentation from which relevant concepts were found (e.g., diabetic foot exam).

It can be demonstrated that as much as a two-fold improvement in patient compliance with quality measures such as diabetic kidney disease screening could be achieved by simply including data mined from the clinical narrative in the measure calculation. There was no change in clinical workflow or care delivery.

The MINE Quality Optimizer QMREF more accurately uncovers services completed for a patient in an automated fashion without the need for a costly chart review. In addition, a healthcare organization could potentially gain more revenue where measure performance is tied to reimbursement.

Figure 10:
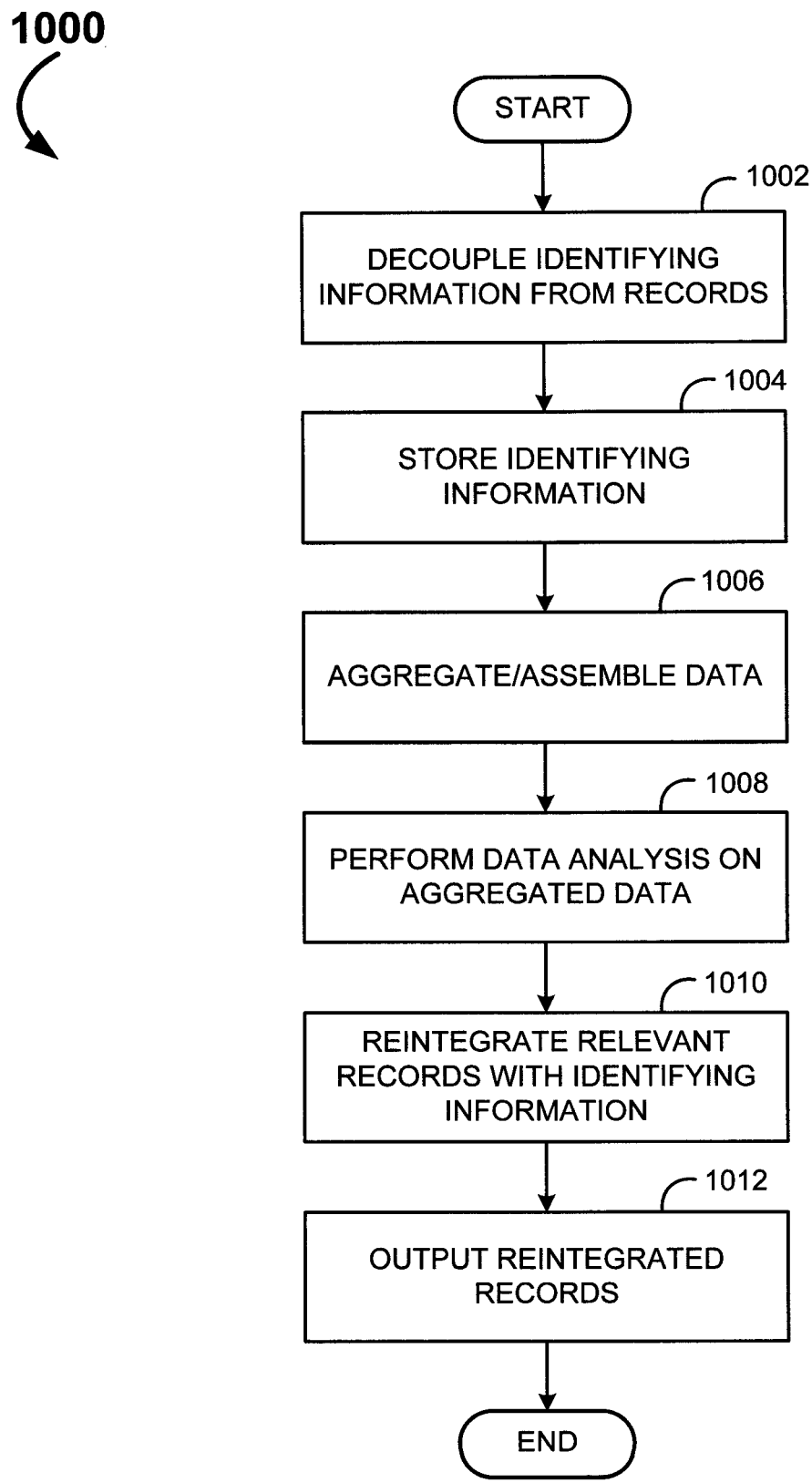
FIGS. 10 and 11 illustrate exemplary process flows for the analysis of medical information, and application of said analysis to individual patients, in accordance with some embodiments.

FIG. 10 illustrates an exemplary process flow 1000 for the analysis of medical information, and application of said analysis to individual patients, in accordance with some embodiments. In this process patient health records are decoupled from the identifying information from non-identifying records (at 1002). Identifying data may include patient name, social security number, contact information, or the like. Identifying information may also include PHI as defined by HIPAA including dates and potential findings, as per relevant statutes. The identifying information is then stored for later retrieval (at 1004). In some embodiments, the decoupled identifying information is encrypted on a per patient per organization basis. Individual encryption, by patient, enables granular access to individual patient health record upon reintegration. In some cases, it may also be desirable to group identifying information by a relevant cohort, and encrypt the group identifying information. This "group level" encryption may have utility where a group is undergoing clinical trials or have some other common procedure or risk factor (such as environmental exposure).

The de-identified information may be indexed, as described above, and encrypted, in some embodiments. The indexed data allows for very rapid searching. Additionally, the deidentified information may be output to external entities, such as academic institutions, for research or analysis purposed without violating patient privacy.

Figure 11:
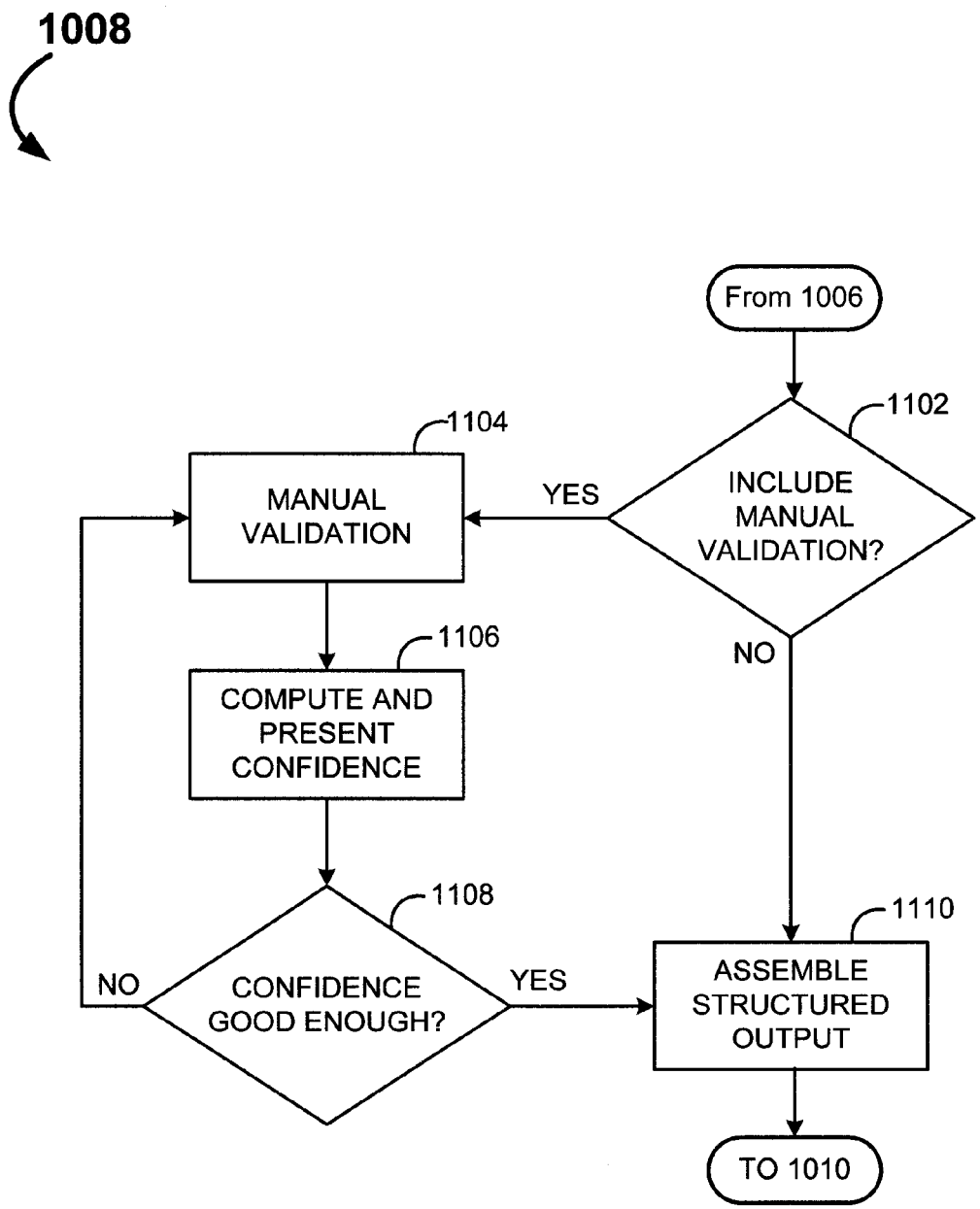

The deidentified data may be aggregated by the MINE QMREF (at 1006), and analyzed for relevant information (at 1008). Turning briefly to FIG. 11, the process for data analysis is illustrated in further detail. Text is structured with concepts relevant to quality measurement (diseases, procedures, measurements, etc.). If manual validation is required (at 1102), then the output is validated (at 1104). The confidence of the measure value is computed and presented (at 1106). The validation and confidence computation steps can be repeated as needed if it is determined that confidence is not sufficient (at 1108).

If manual validation is not required (at 1102), or if the confidence is acceptable, then structured data and extracted structure can be combined (into structured output at 1110). The outputted structured data may be analyzed by the MINE, or may be output to a third party for analysis. Analysis of the deidentified indices may result in the identification of at least one relevant "event". A clinical event is any granular clinical concept (apixion)—associated with a timestamp of when it happened, it may optionally have a where (location) and whom (clinical actors). An example of a pair of event is a "a myocardial infarction for patient X four years ago at home treated by the ER physician Y at the regional hospital". This can be decomposed into two events: an MI for patient X at home four years ago (relative to the document date) and treatment of MI for patient X at the regional hospital by ER physician Y also four years ago (relative to the document date).

Returning to FIG. 10, after analysis, the records may be reintegrated with the identifying information (at 1010). This reintegration ensures that the records may be shared with care providing organization. Further, by reintegrating the identifying information after analysis, the patients may still be able to take advantage of the analysis results. Reintegration may also be employed when additional information needs to be meta-tagged for a specific patient or additional data needs to be added to a specific patient. It is also possible that the reintegrated patient information may be subsequently decoupled from the patient identifying information in order to update indexes.

Lastly, when desired, the reintegrated records may be output (at 1012) for acting upon the findings, at the patient level, by the health provider organization. In some embodiments, each patient's data is encrypted individually in order to ensure advanced security, and compliance with privacy laws. The individual encryption may be generated and managed based upon information found in the patient's charts. As each chart is different, this enables the system to ensure each record is encrypted uniquely. The system may also keep track of each encrypted record in order to enable decryption and data access at later times.

Presentation of Confidence

In some embodiments, confidence level translates into a lower bound on the probability that a reported outcome (e.g., a measure numerator) is >=the actual outcome. Actual outcome is the value that would be determined in a complete manual audit (a.k.a. 100% audit).

Figure 12:
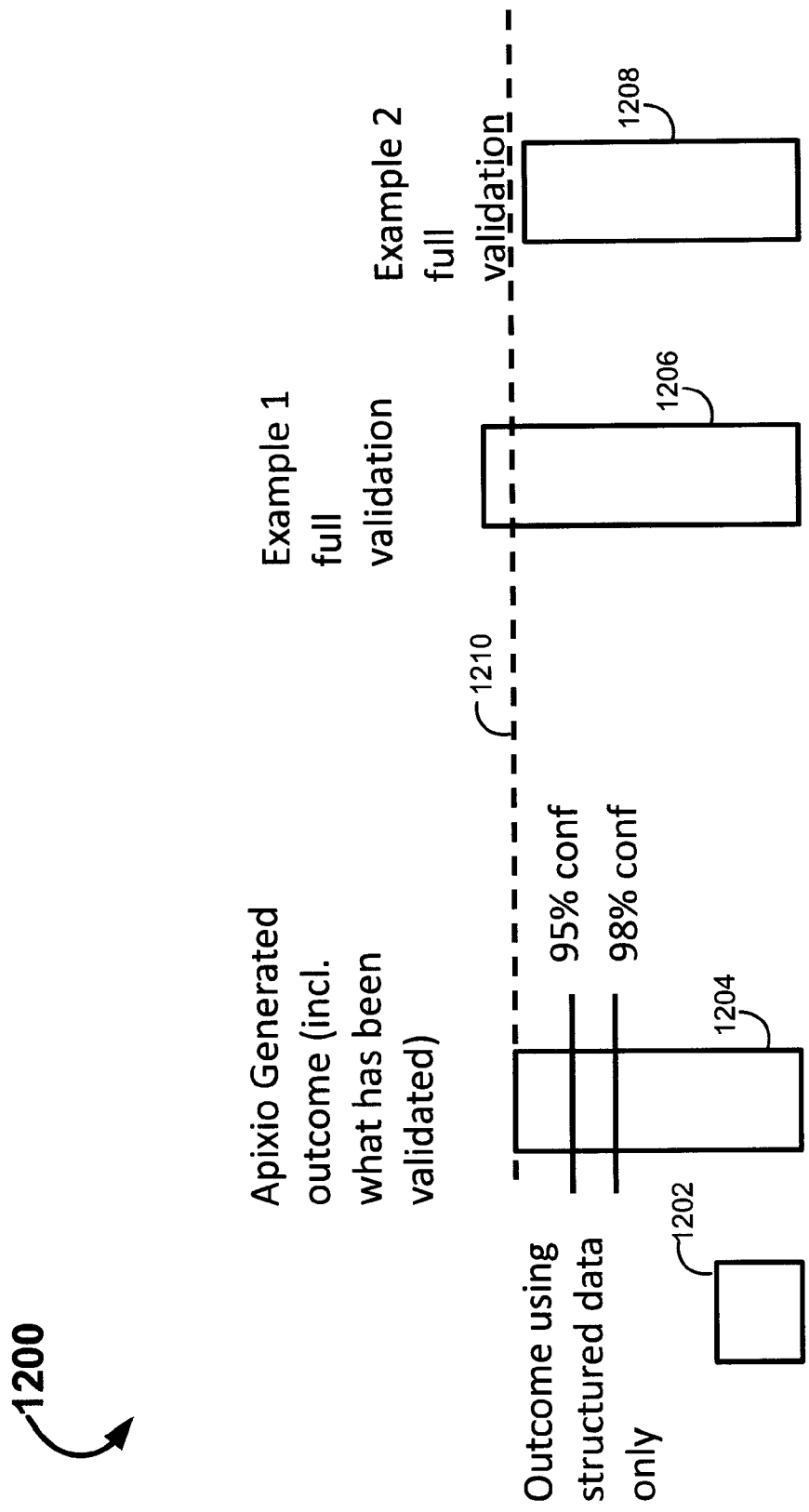
FIGS. 12 and 13 illustrate exemplary outcome validations for the MINE 112 of FIG. 1, in accordance with some embodiments.
Figure 13:
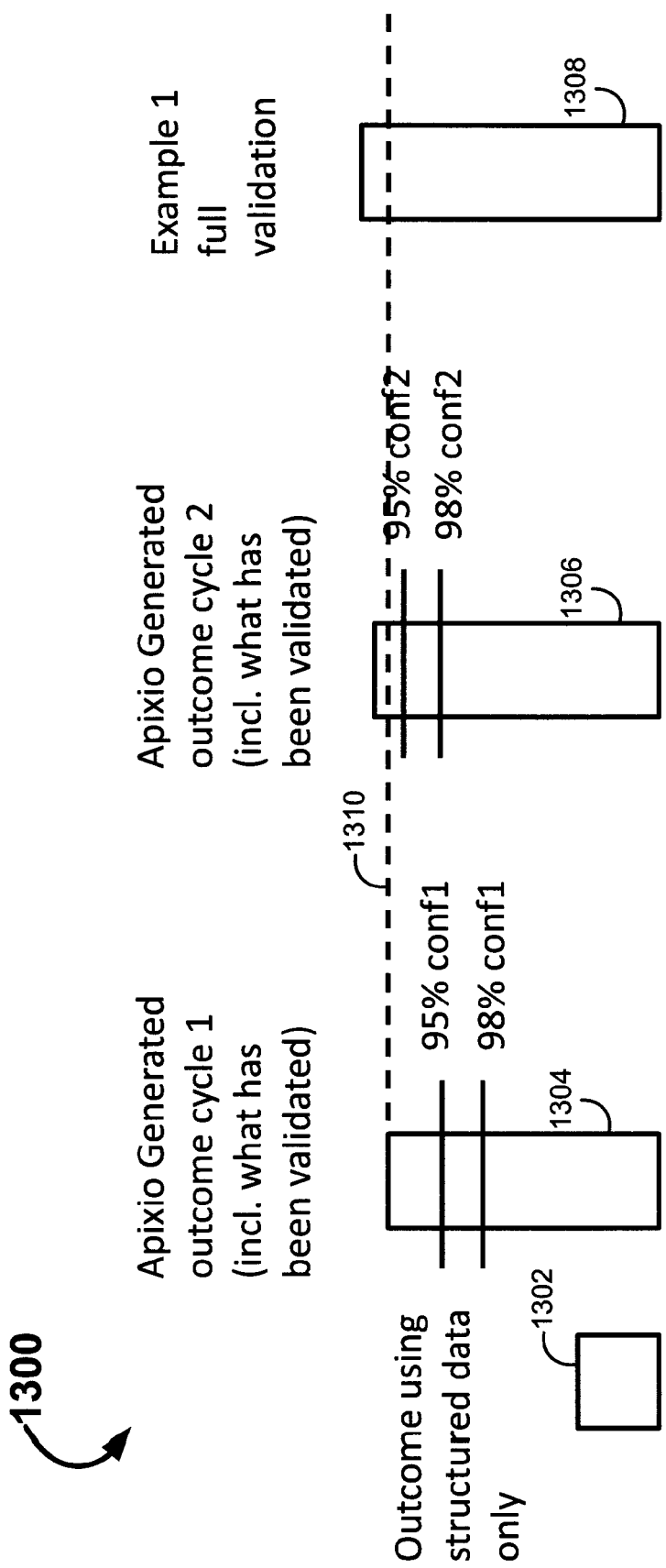

What is presented to the user is the value computed by the algorithm output adjusted by any validated results ("generated outcome") and the outcome value that corresponds to a specific confidence level. For example, as illustrated by FIGS. 12 and 13, the user may set the confidence level to a specific value, such as 95%, and see the outcome that this corresponds to. In these illustrations the outcomes using structured data are illustrated at 1202 and 1302. By optimizing outcomes, as illustrated at 1204, 1304 and 1306, respectively, confidence intervals may likewise be calculated. Lastly, full validation outcomes are illustrated at 1206, 1208 and 1308, respectively. The presentation and configuration of confidence intervals allows organizations to choose between 100% audits, partial audits (enough to support the confidence interval of choice) and/or full automated calculations (if automated precision and recall are such that the desired confidence interface is automatically achieved).

Computation of Outcomes Corresponding to Various Confidence Levels

In an exemplary computation: Assume 100% audit yields an outcome p (expressed as a rate from 0-1). Then Hoeffding's inequality gives the equation:

$$Pr(\epsilon, n) \leq e^{-2\epsilon^2 n}$$

where $\epsilon$ is difference in measured rate from p, and
n is number of included patients.

Set $Pr(\epsilon,n)$ to 0.05 for 95% confidence level, put in n (the number of patients tested for outcome) and solve for $\epsilon$ to get outcome value corresponding to confidence level.

Other embodiments account for systematic errors which are introduced when precision and recall are less than 100%.

IV. Example Screenshots

Figure 14:
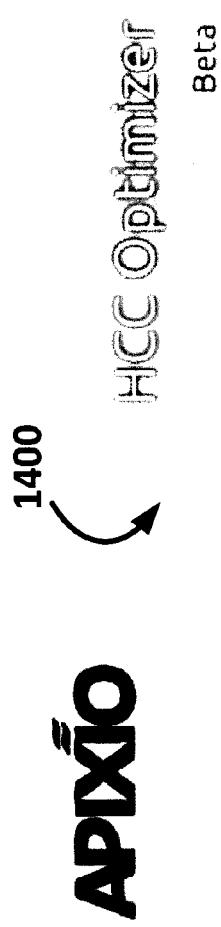

FIG. 14 illustrates an example screenshot (at 1400) of the HCC Optimizer. In this example screenshot, the patients are listed. A search function provides the ability to perform natural language queries of the health records. The system also provides the user potential opportunities, accepted opportunities and possible improvements in optimization.

FIG. 15 is a screenshot (at 1500) where a patient record has been opened. The system displays patient identifying information (name, DOB, etc.). Additionally, the system lists individual records for the patient that may be further accessed. In this example record, the patient has an office visit and progress note available. The office visit and progress note are specific instances that are relevant to the objectives of the organization. For example—if you are looking for diabetics (relevant to the organization) these documents may be provided, even though the patient may have many records In FIG. 16, the office visit note has been accessed. The example screenshot (at 1600) displays the results of the office visit. In some embodiments, medical concepts of importance relating to query may be highlighted for the user. All patient records may be analyzed via the processes described above in order to optimize patient care, and identify correlations that through population analysis.

V. System Embodiments

Figure 17A:
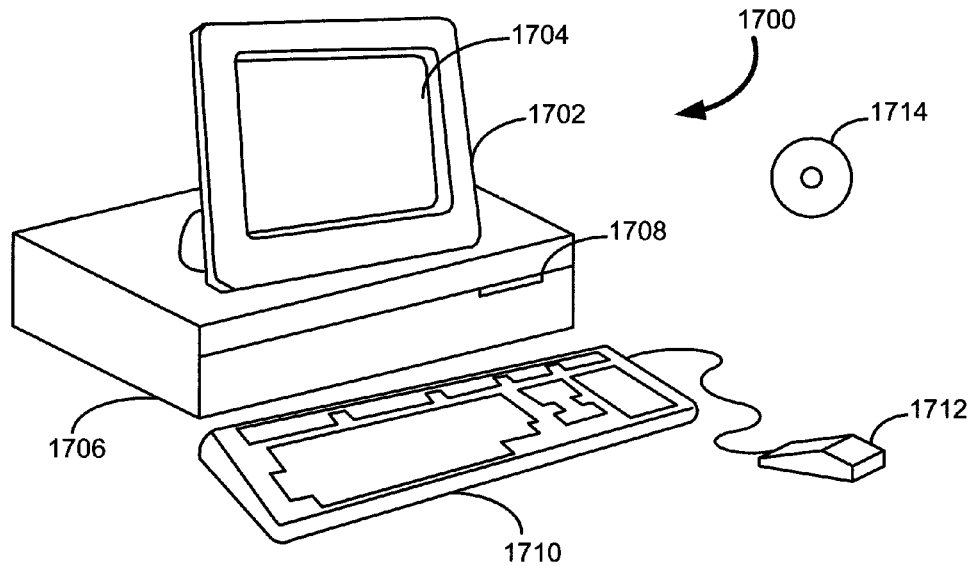
FIGS. 17A and 17B illustrate systems configured to embody embodiments of the disclosed medical information systems, in accordance with some embodiments.
Figure 17B:
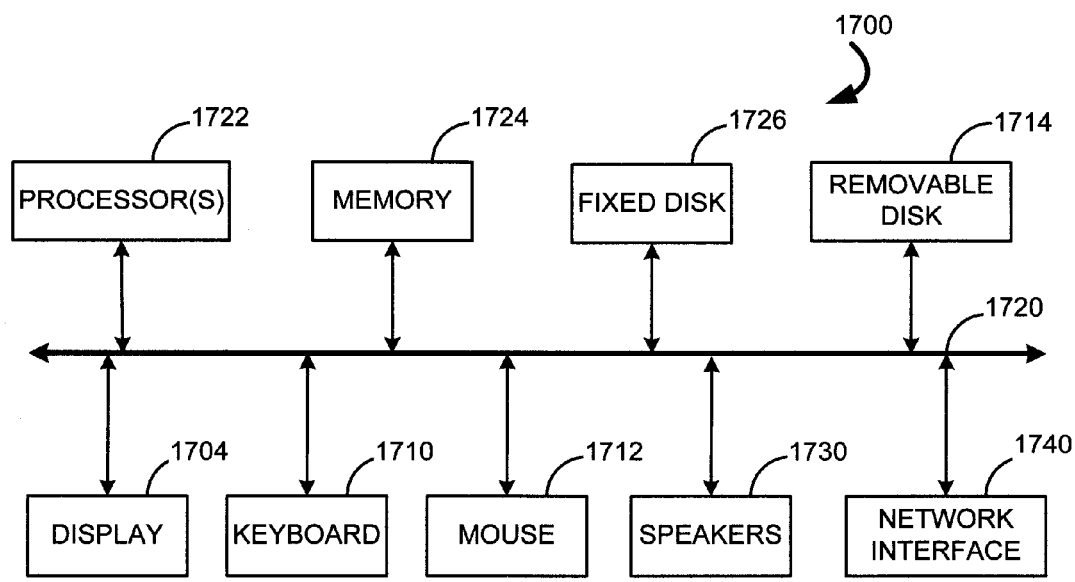

FIGS. 17A and 17B illustrate a Computer System 1700, which is suitable for implementing embodiments of the present invention. FIG. 17A shows one possible physical form of the Computer System 1700. Of course, the Computer System 1700 may have many physical forms ranging from a printed circuit board, an integrated circuit, and a small handheld device up to a huge super computer. Computer system 1700 may include a Monitor 1702, a Display 1704, a Housing 1706, a Disk Drive 1708, a Keyboard 1710, and a Mouse 1712. Disk 1714 is a computer-readable medium used to transfer data to and from Computer System 1700.

FIG. 17B is an example of a block diagram for Computer System 1700. Attached to System Bus 1720 are a wide variety of subsystems. Processor(s) 1722 (also referred to as central processing units, or CPUs) are coupled to storage devices, including Memory 1724. Memory 1724 includes random access memory (RAM) and read-only memory (ROM). As is well known in the art, ROM acts to transfer data and instructions uni-directionally to the CPU and RAM is used typically to transfer data and instructions in a bi-directional manner. Both of these types of memories may include any suitable of the computer-readable media described below. A Fixed Disk 1726 may also be coupled bi-directionally to the Processor 1722; it provides additional data storage capacity and may also include any of the computer-readable media described below. Fixed Disk 1726 may be used to store programs, data, and the like and is typically a secondary storage medium (such as a hard disk) that is slower than primary storage. It will be appreciated that the information retained within Fixed Disk 1726 may, in appropriate cases, be incorporated in standard fashion as virtual memory in Memory 1724. Removable Disk 1714 may take the form of any of the computer-readable media described below.

Processor 1722 is also coupled to a variety of input/output devices, such as Display 1704, Keyboard 1710, Mouse 1712 and Speakers 1730. In general, an input/output device may be any of: video displays, track balls, mice, keyboards, microphones, touch-sensitive displays, transducer card readers, magnetic or paper tape readers, tablets, styluses, voice or handwriting recognizers, biometrics readers, or other computers. Processor 1722 optionally may be coupled to another computer or telecommunications network using Network Interface 1740. With such a Network Interface 1740, it is contemplated that the Processor 1722 might receive information from the network, or might output information to the network in the course of performing the above-described medical records management and analysis. Furthermore, method embodiments of the present invention may execute solely upon Processor 1722 or may execute over a network such as the Internet in conjunction with a remote CPU that shares a portion of the processing.

In addition, embodiments of the present invention further relate to computer storage products with a computer-readable medium that have computer code thereon for performing various computer-implemented operations. The media and computer code may be those specially designed and constructed for the purposes of the present invention, or they may be of the kind well known and available to those having skill in the computer software arts. Examples of computer-readable media include, but are not limited to: magnetic media such as hard disks, floppy disks, and magnetic tape; optical media such as CD-ROMs and holographic devices; magneto-optical media such as floptical disks; and hardware devices that are specially configured to store and execute program code, such as application-specific integrated circuits (ASICs), programmable logic devices (PLDs) and ROM and RAM devices. Examples of computer code include machine code, such as produced by a compiler, and files containing higher level code that are executed by a computer using an interpreter.

While this invention has been described in terms of several embodiments, there are alterations, modifications, permutations, and substitute equivalents, which fall within the scope of this invention. Although sub-section titles have been provided to aid in the description of the invention, these titles are merely illustrative and are not intended to limit the scope of the present invention. It should also be noted that there are many alternative ways of implementing the methods and apparatuses of the present invention. It is therefore intended that the following appended claims be interpreted as including all such alterations, modifications, permutations, and substitute equivalents as fall within the true spirit and scope of the present invention.

What is claimed is:

1. In a medical information navigation engine, a method for quality optimization useful in association with at least one electronic health record system, the method comprising:
   decoupling identifying information from clinical data from at least one electronic health record system, wherein the clinical data includes clinical narrative having discrete data and textual data;
   storing the identifying information, wherein the identifying information is associated with a token in the clinical data;
   indexing the clinical data;
   mining the discrete data and the textual data, wherein the mining includes extracting at least one relevant event from the discrete data and the textual data;
   reintegrating the clinical data with the identifying information using the token; and
   identifying at least one coding opportunity associated with at least one patient condition mined from unstructured clinical data, wherein the at least one patient condition has not yet been associated with one of the patient claims.

2. The method of claim 1 further comprising providing a validation tool for users, including clinicians, to search and view clinical data.

3. The method of claim 1 further comprising at least one of: exporting the at least one relevant event associated with the mined discrete data and textual data; altering treatment of a patient in response to the exported at least one relevant event; meta-tagging information in the clinical data of a specific patient; and adding additional information to the clinical data of the specific patient.

4. The method of claim 1 wherein the at least one relevant event comprises at least one of relevant quality measure, concepts and facts about the patient such as conditions or biometric values or facts about clinical services performed for the patient such as surgical procedures or from the discrete data and the textual data, used for the computation of eligibility for a clinical quality or performance measure, or disease management cohort.

5. The method of claim 1 further comprising aggregating billing data from at least one data source, including an electronic health record system.

6. The method of claim 1 wherein the decoupled identifying information from clinical data is encrypted on a per-patient per organization basis.

7. The method of claim 4 further comprising applying at least one terminology code for at least one of relevant discrete and textual data and fact mined and extracted from the clinical narrative for the purposes of computing either eligibility for or compliance with a quality or performance measure.

8. The method of claim 7 further comprising providing a validation tool for users, including care providers, coders, and care managers, to view the source clinical data from which a fact is mined and extracted and provide feedback regarding the accuracy of the extraction result.

9. The method of claim 1 further comprising providing a view including at least one of patient disease, patient condition, patient risk stratification, patient care quality measure compliance, and patient actionable care gap.

10. The method of claim 9 wherein the patient risk stratification includes co-morbidities associated with at least one of the plurality of patients.

11. The method of claim 1 further comprising presenting at least one optimized target billing code associated with the at least one patient condition.

12. In a medical information navigation engine, a method for quality optimization useful in association with at least one electronic health record system, the method comprising:
    decoupling identifying information from clinical data from at least one electronic health record system, wherein the clinical data includes clinical narrative having discrete data and textual data;
    storing the identifying information, wherein the identifying information is associated with a token in the clinical data;
    indexing the clinical data;
    mining the discrete data and the textual data, wherein the mining includes extracting at least one relevant event from the discrete data and the textual data;
    reintegrating the clinical data with the identifying information using the token;
    decoupling the identifying information from the clinical data for a plurality of electronic health records for a cohort of patients and encrypting the identifying information for the cohort using a single encryption scheme; and
    wherein the cohort includes at least one of demographics, genotype, and phenotype.

13. A medical information navigation engine, useful in association with at least one electronic health record system, the medical information navigation engine comprising:
    a processor configured to decouple identifying information from clinical data from at least one electronic health record system, wherein the clinical data includes clinical narrative having discrete data and textual data;
    a database configured to store the identifying information, wherein the identifying information is associated with a token in the clinical data;
    an indexor configured to index the clinical data;
    the processor further configured to mine the discrete data and the textual data, wherein the mining includes extracting at least one relevant event from the discrete data and the textual data; and
    the processor further configured to reintegrate the clinical data with the identifying information using the token; and
    the processor further configured to identify at least one coding opportunity associated with at least one patient condition mined from unstructured clinical data, wherein the at least one patient condition has not yet been associated with one of the patient claims.

14. The system of claim 13 further comprising a validator configured to provide a validation tool for users, including clinicians, to search and view clinical data.

15. The system of claim 13 wherein the at least one relevant event comprises at least one of relevant quality measure, concepts and facts about the patient such as conditions or biometric values or facts about clinical services performed for the patient such as surgical procedures or from the discrete data and the textual data, used for the computation of eligibility for a clinical quality or performance measure, or disease management cohort.

16. The system of claim 13 wherein the aggregator is further configured to aggregate billing data from at least one data source, including an electronic health record system.

17. The system of claim 15 further comprising a mapper configured to apply at least one terminology code for at least one of relevant discrete and textual data and fact mined and extracted from the clinical narrative for the purposes of computing either eligibility for or compliance with a quality or performance measure.

18. The system of claim 17 further comprising a validator configured to provide a validation tool for users, including care providers, coders, and care managers, to view the source clinical data from which a fact is mined and extracted and provide feedback regarding the accuracy of the extraction result.

19. The system of claim 13 further comprising a visualizer configured to provide a view including at least one of patient disease, patient condition, patient risk stratification, patient care quality measure compliance, and patient actionable care gap.

20. The system of claim 19 wherein the patient risk stratification includes co-modalities associated with at least one of the plurality of patients.

21. The system of claim 13 further comprising an optimizer configured to present at least one optimized target billing code associated with the at least one patient condition.

22. The system of claim 13 further comprising an interface configured to export the relevant event associated with the mined discrete data and textual data.

* * * * *